United States Patent
Preiss-Bloom et al.

(10) Patent No.: US 11,678,923 B2
(45) Date of Patent: *Jun. 20, 2023

(54) ANISOTROPIC BIOCOMPOSITE MATERIAL, MEDICAL IMPLANTS COMPRISING SAME AND METHODS OF TREATMENT THEREOF

(71) Applicant: Ossio Ltd., Binyamina (IL)

(72) Inventors: Orahn Preiss-Bloom, Zichron Yakov (IL); Taly Pnina Lindner, Savyon (IL)

(73) Assignee: OSSIO, LTD., Binyamina (IL)

( * ) Notice: Subject to any disclaimer, the term of this patent is extended or adjusted under 35 U.S.C. 154(b) by 177 days.

This patent is subject to a terminal disclaimer.

(21) Appl. No.: 16/951,109

(22) Filed: Nov. 18, 2020

(65) Prior Publication Data

US 2021/0137576 A1  May 13, 2021

Related U.S. Application Data

(63) Continuation of application No. 15/509,301, filed as application No. PCT/IL2015/050903 on Sep. 7, 2015, now Pat. No. 10,869,708.

(Continued)

(51) Int. Cl.
*A61L 27/50* (2006.01)
*A61B 17/88* (2006.01)
(Continued)

(52) U.S. Cl.
CPC .......... *A61B 17/8875* (2013.01); *A61B 17/16* (2013.01); *A61B 17/1615* (2013.01); *A61B 17/1617* (2013.01); *A61B 17/80* (2013.01); *A61B 17/863* (2013.01); *A61B 17/864* (2013.01); *A61B 17/866* (2013.01); *A61B 17/8625* (2013.01); *A61B 17/8635* (2013.01); *A61F 2/30965* (2013.01); *A61L 27/365* (2013.01); *A61L 27/446* (2013.01);
(Continued)

(58) Field of Classification Search
CPC .............. A61B 17/8625; A61B 17/863; A61B 17/8635; A61B 17/864; A61B 17/866; A61L 27/50
See application file for complete search history.

(56) References Cited

U.S. PATENT DOCUMENTS

| | | |
|---|---|---|
| 4,655,777 A | 4/1987 | Dunn |
| 4,750,905 A | 6/1988 | Koeneman |

(Continued)

FOREIGN PATENT DOCUMENTS

| | | |
|---|---|---|
| CN | 1168105 A | 12/1997 |
| CN | 1214939 A | 4/1999 |

(Continued)

OTHER PUBLICATIONS

Australian Examination Report No. 1 for App. No. AU2017287968, dated Aug. 31, 2021, 3 pages.

(Continued)

*Primary Examiner* — Si Ming Ku
(74) *Attorney, Agent, or Firm* — Graeser Associates International Inc; Dvorak Graeser

(57) ABSTRACT

Reinforced biocomposite materials. According to at least some embodiments, medical implants are provided that incorporate novel structures, alignments, orientations and forms comprised of such reinforced bioabsorbable materials, as well as methods of treatment thereof.

15 Claims, 11 Drawing Sheets

Related U.S. Application Data

(60) Provisional application No. 62/047,023, filed on Sep. 7, 2014.

(51) Int. Cl.

| | | |
|---|---|---|
| *A61L 27/36* | (2006.01) | |
| *A61L 27/44* | (2006.01) | |
| *A61B 17/16* | (2006.01) | |
| *A61F 2/30* | (2006.01) | |
| *A61B 17/86* | (2006.01) | |
| *A61L 31/06* | (2006.01) | |
| *A61L 31/16* | (2006.01) | |
| *A61B 17/80* | (2006.01) | |
| *A61L 31/12* | (2006.01) | |
| *A61L 31/14* | (2006.01) | |
| *A61B 17/04* | (2006.01) | |
| *A61B 17/064* | (2006.01) | |
| *A61B 17/00* | (2006.01) | |
| *A61B 17/12* | (2006.01) | |
| *A61B 17/122* | (2006.01) | |

(52) U.S. Cl.
CPC .............. *A61L 27/50* (2013.01); *A61L 31/06* (2013.01); *A61L 31/128* (2013.01); *A61L 31/148* (2013.01); *A61L 31/16* (2013.01); *A61B 17/0401* (2013.01); *A61B 17/064* (2013.01); *A61B 17/122* (2013.01); *A61B 17/12009* (2013.01); *A61B 2017/00004* (2013.01); *A61B 2017/00964* (2013.01); *A61L 2430/02* (2013.01)

(56) References Cited

U.S. PATENT DOCUMENTS

| | | |
|---|---|---|
| 4,911,718 A | 3/1990 | Lee |
| 5,064,439 A | 11/1991 | Chang |
| 5,181,930 A | 1/1993 | Dumbleton |
| 5,192,330 A | 3/1993 | Chang |
| 5,312,669 A | 5/1994 | Bedard |
| 5,338,772 A | 8/1994 | Bauer |
| 5,522,817 A | 6/1996 | Sander |
| 5,522,904 A | 6/1996 | Moran |
| 5,674,294 A | 10/1997 | Bainville |
| 5,679,299 A | 10/1997 | Gilbert |
| 6,004,650 A | 12/1999 | Schweizer |
| 6,171,338 B1 | 1/2001 | Talja |
| 6,299,649 B1 | 10/2001 | Chang |
| 6,306,140 B1 | 10/2001 | Siddiqui |
| 6,352,667 B1 | 3/2002 | English |
| 6,471,707 B1 | 10/2002 | Miller |
| 6,511,511 B1 | 1/2003 | Slivka |
| 6,602,293 B1 | 8/2003 | Biermann |
| 6,916,321 B2 | 7/2005 | Tenhuisen |
| 7,541,049 B1 | 6/2009 | Toermaelae |
| 7,918,879 B2 | 4/2011 | Yeung |
| 7,947,069 B2 | 5/2011 | Sanders |
| 8,702,716 B1 | 4/2014 | Stein |
| 8,709,055 B2 | 4/2014 | Beyar |
| 8,735,504 B2 | 5/2014 | Clay |
| 8,992,622 B2 | 3/2015 | Ullrich, Jr. |
| 9,186,302 B2 | 11/2015 | Kilway |
| 9,456,890 B2 | 10/2016 | Day |
| 10,926,004 B2 | 2/2021 | Preiss-Bloom |
| 2005/0118326 A1 | 6/2005 | Anfinsen |
| 2005/0177245 A1 | 8/2005 | Leatherbury |
| 2005/0216016 A1 | 9/2005 | Contiliano |
| 2005/0226904 A1 | 10/2005 | Choi |
| 2005/0228500 A1 | 10/2005 | Kim |
| 2006/0020266 A1 | 1/2006 | Cooper |
| 2006/0095134 A1 | 5/2006 | Trieu |
| 2006/0154206 A1 | 7/2006 | Petersson |
| 2006/0178748 A1 | 8/2006 | Dinger, III |
| 2007/0150059 A1 | 6/2007 | Ruberte |
| 2007/0185568 A1 | 8/2007 | Schwartz |
| 2007/0270969 A1 | 11/2007 | Schmid |
| 2007/0282455 A1 | 12/2007 | Luginbuehl |
| 2008/0255561 A1 | 10/2008 | Tormala |
| 2009/0112317 A1 | 4/2009 | Li |
| 2009/0240337 A1 | 9/2009 | Myung |
| 2009/0258965 A1 | 10/2009 | Lassila |
| 2009/0304761 A1 | 12/2009 | Rabiei |
| 2010/0119564 A1 | 5/2010 | Kasuga |
| 2010/0121463 A1 | 5/2010 | Toermaelae |
| 2010/0168798 A1 | 7/2010 | Clineff |
| 2011/0098826 A1 | 4/2011 | Mauck |
| 2011/0166659 A1 | 7/2011 | Luginbuehl |
| 2011/0282395 A1 | 11/2011 | Beyar |
| 2012/0016373 A1 | 1/2012 | Impellizzeri |
| 2012/0040015 A1 | 2/2012 | Lehtonen |
| 2012/0040137 A1 | 2/2012 | Palasis |
| 2012/0191214 A1 | 7/2012 | Nies |
| 2012/0265206 A1 | 10/2012 | Jang |
| 2013/0144400 A1 | 6/2013 | Day |
| 2013/0204368 A1 | 8/2013 | Prevost |
| 2013/0218291 A1 | 8/2013 | Giorno |
| 2013/0296500 A1 | 11/2013 | Clay |
| 2013/0317555 A1 | 11/2013 | Schaller |
| 2015/0238655 A1 | 8/2015 | Jongpaiboonkit |
| 2015/0289979 A1 | 10/2015 | Gabele |
| 2016/0011369 A1 | 1/2016 | Doyle |
| 2016/0113695 A1 | 4/2016 | Globerman |
| 2016/0278789 A1 | 9/2016 | Garvey |
| 2017/0181785 A1 | 6/2017 | Beyar |
| 2017/0246356 A1 | 8/2017 | Preiss-Bloom |
| 2021/0161571 A1 | 6/2021 | Haziza |
| 2021/0299332 A1 | 9/2021 | Dias |
| 2022/0008615 A1 | 1/2022 | Cige |

FOREIGN PATENT DOCUMENTS

| | | |
|---|---|---|
| CN | 1371664 A | 10/2002 |
| CN | 1565396 A | 1/2005 |
| CN | 1593356 A | 3/2005 |
| CN | 1953719 A | 4/2007 |
| CN | 101420991 A | 4/2009 |
| CN | 101437467 A | 5/2009 |
| CN | 101790559 B | 7/2010 |
| CN | 101942709 A | 1/2011 |
| CN | 102281907 A | 12/2011 |
| CN | 102395329 A | 3/2012 |
| CN | 102421463 A | 4/2012 |
| CN | 102421716 A | 4/2012 |
| CN | 103747813 A | 4/2014 |
| CN | 104188706 A | 12/2014 |
| EP | 0373294 A2 | 6/1990 |
| EP | 1716874 A2 | 11/2006 |
| EP | 2243500 A1 | 10/2010 |
| EP | 2243749 A1 | 10/2010 |
| EP | 2292166 A1 | 3/2011 |
| EP | 17819487 | 6/2017 |
| EP | 3236866 | 11/2017 |
| EP | 3320877 | 5/2018 |
| EP | 3320877 A1 | 5/2018 |
| JP | 6415040 | 1/1989 |
| JP | H02121652 | 5/1990 |
| JP | 2002501418 A | 1/2002 |
| JP | 2004160157 | 6/2004 |
| JP | 2008200510 | 9/2008 |
| JP | 2009541568 | 11/2009 |
| JP | 2010526200 | 7/2010 |
| JP | 2012524569 | 10/2012 |
| WO | 9609014 | 3/1996 |
| WO | 9609014 A1 | 3/1996 |
| WO | 1996009014 | 3/1996 |
| WO | 9819616 | 5/1998 |
| WO | 9819617 A1 | 5/1998 |
| WO | 9853768 | 12/1998 |
| WO | 9853768 A1 | 12/1998 |
| WO | 0132072 | 5/2001 |
| WO | 2005077039 A2 | 8/2005 |
| WO | 2005077039 A3 | 8/2005 |

(56) References Cited

FOREIGN PATENT DOCUMENTS

| WO | 2008095046 | A2 | 8/2008 |
|---|---|---|---|
| WO | 2010122019 | A1 | 10/2010 |
| WO | 2010122098 | A2 | 10/2010 |
| WO | 2013116624 | A1 | 8/2013 |
| WO | 2016035088 | | 3/2016 |
| WO | 2016035088 | A1 | 3/2016 |
| WO | 2016103049 | | 6/2016 |
| WO | 2017155956 | A1 | 9/2017 |
| WO | 2018002917 | | 1/2018 |

OTHER PUBLICATIONS

Chinese Office Action (including English translation) for App. No. CN201780025291.1, dated Aug. 10, 2021, 12 pages.
European Patent Office Communication pursuant to Article 94(3) EPC for App. No. EP17819487.4, dated Jun. 21, 2021, 5 pages.
Extended European Search Report for App. No. EP18890927.9, dated Jul. 27, 2021, 7 pages.
Chinese Third Office Action (with English translation) for App. No. CN201780053086.6, dated Feb. 16, 2022, 13 pages.
European Patent Office Communication pursuant to Article 94(3) EPC for App. No. EP17763876.4, dated Jan. 4, 2022, 8 pages.
Japanese Office Action (including English translation) for App. No. JP2018-567587, dated Jan. 5, 2022, 5 pages.
Korean Office Action (including English translation) for App. No. KR10-2019-7001863, dated Jan. 20, 2022, 13 pages.
Office Action (Notice of Allowance and Fees Due (PTOL-85)) dated Jan. 18, 2022 for U.S. Appl. No. 16/637,363 (pp. 1-9).
Office Action (Notice of Allowance and Fees Due (PTOL-85)) dated Feb. 8, 2022 for U.S. Appl. No. 16/311,784 (pp. 1-6).
Office Action (Notice of Allowance and Fees Due (PTOL-85)) dated Feb. 22, 2022 for U.S. Appl. No. 16/311,784 (pp. 1-3).
Canadian Office Action for App. No. CA2,955,392, dated Sep. 27, 2021, 15 pages.
Chinese Office Action (with English translation) for App. No. CN201780053086.6, dated Oct. 19, 2021, 15 pages.
Chinese Office Action for App. No. CN201880057783.3, dated Dec. 2, 2021, 15 pages.
Indian Examination Report for App. No. IN201827049363, dated Nov. 18, 2021, 5 pages.
Office Action dated Sep. 23, 2021 for U.S. Appl. No. 16/311,784 (pp. 1-11).
Arthrex Inc., "BioComposite Interference Screws—A Stronger turn in ACL/PCL Reconstruction", Scientific Research and Development, (20100000), URL: http://www.arthrex.com/knee/biocomposite-interference-screws. (6 pages).
Australian Examination Report No. 1 for Application No. 2015310510, dated Aug. 10, 2019, 6 pages.
Australian Examination Report No. 1 for Application No. AU2015370600, dated Oct. 2, 2019, 3 pages.
Australian Examination Report No. 2 for Application No. AU2015310510, dated Dec. 1, 2019, 3 pages.
Australian Examination Report No. 2 for Application No. AU2015370600, dated Jan. 29, 2020, 2 pages.
Brazilian Search Report (with English language translation) for App No. BR112017001049-6, dated Apr. 8, 2020, 8 pages.
Brazilian Technical Report (with English language translation) for App No. BR112017012508-0, dated Apr. 8, 2020, 7 pages.
Chinese Office Action (with English language translation) for App No. CN201580070362.0, dated May 20, 2020, 9 pages.
Chinese Office Action (with English language translation) for Application No. 201580036606.3, dated Mar. 12, 2019, 13 pages.
Chinese Office Action (with English language translation) for Application No. CN201580036606.3, dated Oct. 25, 2019, 9 pages.
Chinese Office Action (with English language translation) for Application No. CN201580037255.8, dated Aug. 26, 2019, 16 pages.
Chinese Office Action (with English language translation) for Application No. CN201580070362.0, dated Aug. 29, 2019, 10 pages.
Chinese Office Action dated Jul. 13, 2018 for corresponding CN Patent Application No. 201580037255.8, 9 pages.
Chinese Office Action for Appl. No. 201580037255.8, dated Mar. 26, 2019, 7 pages.
Corrected Notice of Allowability dated Oct. 19, 2020 for U.S. Appl. No. 16/081,605 (pp. 1-9).
Corrected Notice of Allowability dated Oct. 7, 2020 for U.S. Appl. No. 15/509,301 (pp. 1-6).
European Patent Office Communication pursuant to Article 94(3) EPC for App. No. EP17763876.4, dated Aug. 19, 2020, 9 pages.
European Search Report and Written Opinion dated Jun. 12, 2018 for EP Application No. 158720441, 5 pages.
European Search Report dated Oct. 16, 2019 for EP Application No. 17763876.4, 11 pages.
European Search Report for EP15838477.6 dated Mar. 5, 2018, 5 pages.
Extended European Search Report for Application No. EP17819487.4, dated Feb. 4, 2020, 7 pages.
Extended European Search Report for Application No. EP19200585.8, dated Feb. 28, 2020, 8 pages.
Hyon et al., "Effects of Residual Monomer on the Degradation of DL-Lactide Polymer" Polymer International 46 (1998) 196-202.
International Search Report issued in PCT/IL2019/050843, dated Nov. 6, 2019, 3 pages.
IP Office of Singapore Written Opinion for Application No. SG11201610671P, dated Aug. 14, 2019, 5 pages.
Japanese Office Action (with English language translation) for Application No. 2017-504425, dated May 28, 2019, 7 pages.
Japanese Office Action (with English language translation) for Application No. JP2017-504425, dated Jan. 7, 2020, 6 pages.
Japanese Office Action (with English language translation) for Application No. JP2017-527796, dated Nov. 5, 2019, 6 pages.
Kulkova J. et al. "Hydroxyapatite and bioactive glass surfaces for fiber reinforced composite implants via surface ablation by Excimer laser" (2017) Journal of the Mechanical Behavior of Biomedical Materials, vol. 75, pp. 89-96, DOI: 10.1016/j.jmbbm.2017.07.005 (published on-line Jul. 4, 2017).
Notice of Allowance dated Aug. 20, 2020 for U.S. Appl. No. 15/509,301 (pp. 1-9).
Notice of Allowance dated Aug. 28, 2020 for U.S. Appl. No. 16/081,605 (pp. 1-14).
Notice of Allowance dated Oct. 22, 2020 for U.S. Appl. No. 15/523,389 (pp. 1-6).
Office Action dated Aug. 5, 2019 for U.S. Appl. No. 15/509,274 (pp. 1-19).
Office Action dated Dec. 26, 2019 for U.S. Appl. No. 15/509,274, 18 pages.
Office Action dated Feb. 10, 2020, for U.S. Appl. No. 16/081,605 (pp. 1-17).
Office Action dated Jan. 13, 2020 for U.S. Appl. No. 15/523,389 (pp. 1-11).
Office Action dated Jul. 13, 2020 for U.S. Appl. No. 15/523,389 (pp. 1-12).
Office Action dated Nov. 18, 2019 for U.S. Appl. No. 16/081,605 (pp. 1-19).
Office Action dated Nov. 19, 2020 for U.S. Appl. No. 16/311,784 (pp. 1-14).
Office Action dated Nov. 7, 2019 for U.S. Appl. No. 15/523,389 (pp. 1-11).
Scholz et al., "The use of composite materials in modern orthopaedic medicine and prosthetic devices: A review", Composites Science and Technology, Elsevier, Amsterdam, NL, www.elsevier.com/locate/compscitech, vol. 71, No. 16 (2011) pp. 1791-1803.
Search report for parent PCT application No. PCT/IL2015/050903, dated Jan. 7, 2016 (13 pages).
Supplementary European Search Report for EP15837823 dated Mar. 28, 2018, 6 pgs.

(56) References Cited

OTHER PUBLICATIONS

Wang et al., "Promising Poly(E-caprolactone) composite reinforced with weft-knitted polyester for small-diameter vascular graft application", Advances in Materials Science and Engineering, 2014, vol. 2014, p. 273891, 11 pages.
Wegener et al., "Microstructure, cytotoxicity and corrosion of powder-metallurgical iron alloys for biodegradable bone ematerials", Materials Science & Engineering. B. Advanced Functional Solid-State Materials, 2011, vol. 176, No. 20, p. 1789-1796.
Canadian Office Action issued in App. No. CA2,955,392, dated May 31, 2022, 4 pages.
Chinese Office Action (with English translation) for App. No. CN201780053086.6, dated May 7, 2022, 21 pages.
Composites Encyclopedia, Wo Dingzhu et al., pp. 519-520, Beijing: Chemical Industry Press, Jan. 2001, (pp. 7-12).
English translation of Chinese Office Action issued in App. No. CN201780025291.1, dated Apr. 9, 2022, 6 pages.
English translation of Chinese Office Action issued in App. No. CN201880057783.3, dated Dec. 2, 2021, 11 pages.
Indian Examination Report issued in App. No. IN202027011276, dated Apr. 27, 2022, 7 pages.
Office Action (Notice of Allowance and Fees Due (PTOL-85)) dated Mar. 29, 2022 for U.S. Appl. No. 16/637,363 (pp. 1-6).
Australian Examination Report No. 1 for App. No. AU2017287968, dated Feb. 12, 2021, 4 pages.
Chinese Office Action (including English translation) for App. No. CN201780025291.1, dated Jan. 28, 2021,12 pages.
Chinese Office Action for App. No. CN201780053086.6, dated Feb. 18, 2021, 23 pages.
English translation of Japanese Office Action for App. No. JP2018-567587, dated Mar. 23, 2021, 4 pages.
Office Action dated Apr. 7, 2021 for U.S. Appl. No. 16/311,784 (pp. 1-11).
Wei Junjie, "Medical Organic Chemistry Learning Guide", p. 300, Heilongjiang Science and Technology Press, Jan. 19.
Li Sijiao, "Modern Chromatographic Analysis", p. 118, National Defense Industry Press, Jun. 2014.
Extended European Search Report for App. No. EP18853365.7, dated May 4, 2021, 7 pages.
Corrected Notice of Allowability dated Dec. 23, 2020 for U.S. Appl. No. 15/523,389 (pp. 1-3).
C. Capelaa, S. E. Oliveiraa, J. Pestanaa, J.A.M. Ferreira, "Effect of fiber length on the mechanical properties of high dosage carbon reinforced", Procedia Structural Integrity 5 (2017) 539-546.
Chinese Office Action (including English translation) issued in App. No. CN201880057783.3, dated Aug. 2, 2022, 16 pages.
English translation of Japanese Office Action issued in App. No. JP2018-567587, dated Jul. 5, 2022, 4 pages.
Feih, S., Wonsyld, K., Minzari, D., Westermann, P., & Lilholt, H. (2004). Testing Procedure for the Single Fiber Fragmentation Test. Risø National Laboratory. Denmark. Forskningscenter Risoe. Risoe-R No. 1483(EN) 31 pages.
Ferri JM et al., "The effect of beta-tricalcium phosphate on mechanical and thermal performances of poly(lactic acid)", J Composite Materials 2016; 0(0): 1-10.
Japanese Office Action (includig English translation) issued in App. No. JP2020-511984, dated Aug. 2, 2022, 13 pages.
Juan David Vanegas-Jaramillo, Iván David Patiño-Arcilaa, Fragmentation model for the tensile response of unidirectional composites based on the critical number of fiber breaks and the correction of the fiber-matrix interfacial strength Latin American Journal of Solids and Structures, 2019, 16(7), e217, 27 pages.
Jurij Štalc, Luke D. Cicchinelli, Stuart Miller, Carolyn M. Sofka, Martinus Richter Fiber-reinforced fixation implant for proximal interphalangeal joint arthrodesis shows advanced implant biointegration at 2-year follow-up Foot Ankle Surg. Jun. 23, 2022:S1268-7731(22)00117-5, 7 pages.
Korean Office Action issued in App. No. KR10-2017-7018042, dated Aug. 17, 2022, 7 pages.
Miwa, M., Horiba, N. Effects of fiber length on tensile strength of carbon/glass fiber hybrid composites. Journal of Materials Science 29, 973-977 (1994).
Miwa, M., Ohsawa, T., and Tahara, K. (1980), Effects of fiber length on the tensile strength of epoxy/glass fiber and polyester/glass fiber composites. J. Appl. Polym. Sci., 25: 795-807 (Abstract).
P. Amuthakkannan, V. Manikandan, J.T. Winowlin Jappes, M. Uthayakumar Effect of Fibre Length and Fibre Content on Mechanical Properties of Short Basalt Fibre Reinforced Polymer Matrix Composites Materials Physics and Mechanics 16 (2013) 107-117.
Polymer-Matrix Composites: Structure and Processing Deborah D.L. Chung, in Carbon Composites (Second Edition), 2017 3.3.4 Fiber Fragmentation Testing, 13 pages.
Rodricks CW, Greenfeld I, Fiedler B, Wagner HD. Fragmentation of Beaded Fibres in a Composite. Materials (Basel). Jan. 24, 2022;15(3):890, 22 pages.
Shia, David & Hui, Chung Yuen & Phoenix, S . . . (2000). Statistics of fragmentation in a single-fiber composite under matrix yielding and debonding with application to the strength of multi-fiber composites. Composites Science and Technology. 60. 2107-2128. 10.1016/S0266-3538(00)00115-9. (Abstract) 7 pages.
Shiqiang Deng, Lin Ye, Yiu-Wing Mai, Hong-Yuan Liu, Evaluation of fibre tensile strength and fibre/matrix adhesion using single fibre fragmentation tests, Composites Part A: Applied Science and Manufacturing, vol. 29, Issue 4, 1998, pp. 423-434 (Abstract).
Website downloaded Aug. 23, 2022 (https://www.orthobullets.com/basic-science/9062/material-properties) 11 pages.
Extended European Search Report issued in App. No. EP22185127, dated Dec. 15, 2022, 9 pages.
Office Action (Non-Final Rejection) dated Nov. 7, 2022 for U.S. Appl. No. 17/152,165 (pp. 1-15).
Office Action (Non-Final Rejection) dated Nov. 25, 2022 for U.S. Appl. No. 16/770,091 (pp. 1-22).

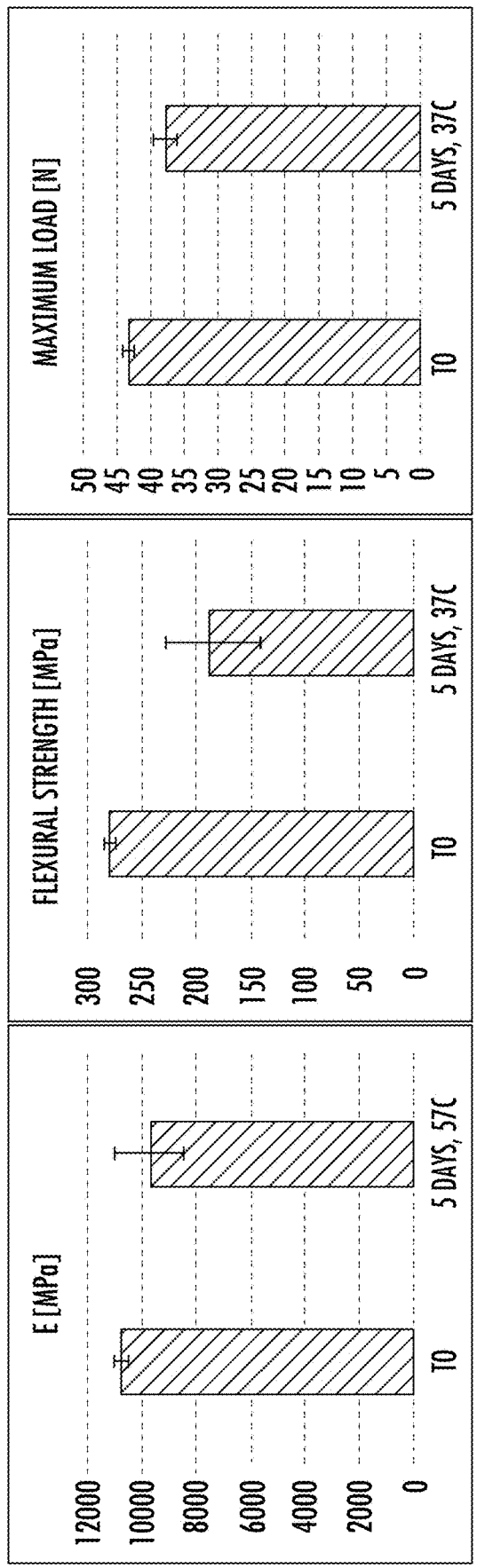

ANISOTROPIC BIOCOMPOSITE MATERIAL, MEDICAL IMPLANTS COMPRISING SAME AND METHODS OF TREATMENT THEREOF

FIELD OF THE INVENTION

The present invention is of anisotropic biocomposite material, medical implants comprising same and methods of treatment thereof, and in particular to such material, implants and methods of treatment that have medical applications.

BACKGROUND OF THE INVENTION

The mechanical strength and modulus (approximately 3-5 GPa) of non-reinforced resorbable polymers is insufficient to support fractured cortical bone, which has an elastic modulus in the range of approximately 15-20 GPa. For example, in an article the bending modulus of human tibial bone was measured to be about 17.5 GPa (Snyder S M Schneider E, Journal of Orthopedic Research, Vol. 9, 1991, pp. 422-431). Therefore, the indications of existing medical implants constructed from resorbable polymers are limited and their fixation usually requires protection from motion or significant loading. These devices are currently only a consideration when fixation of low stress areas is needed (i.e. non-load bearing applications) such as in pediatric patients or in medial malleolar fractures, syndesmotic fixation, maxillofacial, or osteochondral fractures in adults.

A new class of reinforced composite biomaterials (biocomposites) has been recently introduced wherein a bioabsorbable and biocompatible polymer is reinforced by bioabsorbable, biocompatible glass fibers. These materials can achieve improved mechanical properties. These materials also involve a compatibilizer to bind the polymer to the reinforcing fibers. Examples of such materials are described in the following two patent applications, which are included fully herein by reference as if fully set forth herein:
1. Biocompatible composite and its use (WO2010122098)
2. Resorbable and biocompatible fibre glass compositions and their uses (WO2010122019)

These materials have been further described and characterized in publications associated with these patents including
1. Lehtonen T J et al. *Acta Biomaterialia* 9 (2013) 4868-4877
2. Lehtonen T J et al. *J Mech Behavior BioMed Materials.* 20 (2013) 376-386

The development of this class of materials described in the background art has focused on the composition of the materials: the bioabsorbable polymer, the reinforcing mineral fiber, the compatibilizer, and the combinations between them. These compositions have been demonstrated to be capable of achieving mechanical properties superior to the mechanical properties previously achieved with bioabsorbable polymers alone.

However, while material composition is one parameter that can affect mechanical properties of a medical implant, when it comes to composite materials, the material composition does not by itself ensure mechanical properties that are sufficient for the implant to achieve its desired biomechanical function. In fact, reinforced composite medical implants with identical compositions and identical geometries can have vastly different mechanical properties. Furthermore, even within the same implant, mechanical properties can vary greatly between different mechanical axes and between different types of mechanical strength measurements.

SUMMARY OF THE INVENTION

The background art does not teach or suggest biocomposite materials that have one or more desirable mechanical characteristics. The background are also does not teach or suggest such materials that can achieve a desired biomechanical function.

By "biocomposite material" it is meant a composite material that is biologically compatible or suitable, and/or which can be brought into contact with biological tissues and/or which can be implanted into biological materials and/or which will degrade, resorb or absorb following such implantation.

By "biocompatible" it is meant a material that is biologically compatible or suitable, and/or which can be brought into contact with biological tissues, and/or which can be implanted into biological materials.

The present invention, in at least some embodiments, relates to reinforced biocomposite materials which overcome the drawbacks of the background art. According to at least some embodiments, medical implants are provided that incorporate novel structures, alignments, orientations and forms comprised of such reinforced bioabsorbable materials. These medical implants have unique mechanical properties. They have great clinical benefit in that these implants can have mechanical properties that are significant greater than those of the currently available bioabsorbable polymer implants. The term "mechanical properties" as described herein may optionally include one or more of elastic modulus, tensile modulus, compression modulus, shear modulus, bending moment, moment of inertia, bending strength, torsion strength, shear strength, impact strength, compressive strength and/or tensile strength.

According to at least some embodiments, the implants have improved mechanical properties in at least one mechanical axis or parameter as compared with at least one other mechanical axis or parameter within the same implant. The implants can therefore be considered anisotropic. A mechanical axis as defined herein can be any line drawn through the implant, optionally passing through the center of the implant. A mechanical parameter as defined herein can include bending strength and stiffness (resistance to bending force), tensile strength and stiffness (resistance to tensile force), compression strength and stiffness (resistance to compression force), shearing strength and stiffness (resistance to shearing force), or torsional strength and stiffness (resistance to torsional force).

Optionally, the improved mechanical properties in one axis or parameter are increased by at least 50% as compared with another axis or parameter and are preferably increased by at least 100%, more preferably by at least 200%, 300%, 400%, and most preferably by at least 500% or any integral value in between.

Optionally, the improved mechanical properties in one axis or parameter of the implant are alternatively or additionally increased by at least 50% as compared with an implant of identical composition but with amorphous or non-aligned internal structure and are preferably increased by at least 100%, more preferably by at least 200%, 300%, 400%, and most preferably by at least 500% or any integral value in between.

Optionally, the improved mechanical property is strength and the strength in one axis or parameter is increased by at least 50 MPa as compared with another axis or parameter. Preferably, the strength is increased by at least 100 MPa, more preferably by at least 200 MPa, 300 MPa, 400 MPa, and most preferably by at least 500 MPa or any integral value in between.

Optionally, the improved mechanical property is strength and the strength in one axis or parameter of the implant is alternatively or additionally increased by at least 50 MPa as compared with an implant of identical composition but with amorphous or non-aligned internal structure, and preferably are increased by at least 100 MPa, more preferably by at least 200 MPa, 300 MPa, 400 MPa, and most preferably by at least 500 MPa or any integral value in between.

Optionally, the improved mechanical property is elastic modulus and the modulus in one axis or parameter is increased by at least 3 GPa as compared with another axis or parameter. Preferably, the modulus is increased by at least 5 GPa, more preferably by at least 8 GPa, 12 GPa, 16 GPa, and most preferably by at least 20 GPa or any integral value in between.

Optionally, the improved mechanical property is elastic modulus and the modulus in one axis or parameter of the implant is alternatively or additionally increased by at least 3 GPa as compared with an implant of identical composition but with amorphous or non-aligned internal structure. Preferably, the modulus is increased by at least 5 GPa, more preferably by at least 8 GPa, 12 GPa, 16 GPa, and most preferably by at least 20 GPa or any integral value in between.

According to at least some embodiments, anisotropocity of one or more segments of implant in one mechanical axis as compared with amorphous (non-aligned) material is preferably greater than 10%, 50%, 100%, 200%, 300%, 500% or any integral value in between.

According to at least some embodiments, anisotropocity of one or more segments of implant in one mechanical axis as compared with another axis is preferably greater than 10%, 50%, 100%, 200%, 500%, 1000% or any integral value in between.

According to at least some embodiments, there is provided relative higher strength in one mechanical axis as compared with another (e.g. bending over tensile) of 10%, 50%, 100%, 200%, 300% or any integral value in between.

According to at least some embodiments, there is provided relative higher elastic modulus as measured in one mechanical axis as compared with another of 10%, 30%, 50%, 100%, 200% or any integral value in between.

Without wishing to be limited by a closed list or a single hypothesis, the biocomposite implants described herein represent a significant benefit over metal or other permanent implants (including non absorbable polymer and reinforced polymer or composite implants) in that they are absorbable by the body of the subject receiving same, and thus the implant is expected to degrade in the body following implantation. Again without wishing to be limited by a closed list or a single hypothesis, they also represent a significant benefit over prior absorbable implants since they are stronger and stiffer than non-reinforced absorbable polymer implants in at least one mechanical axis. In fact, these reinforced composite polymer materials can even approach the strength and stiffness of cortical bone, making them the first absorbable materials for use in load bearing orthopedic implant applications.

On an underlying level, there is a great difference between the reinforced biocomposite implants and previous implants from metal, plastic, and other traditional medical implant materials. Traditional medical implant materials are isotropic such that their mechanical properties are identical in all axes. This simplifies implant design as the mechanical strength of the implant is determined solely based on the geometry of the implant and the inherent material properties of the material. Without wishing to be limited by a closed list or a single hypothesis, for reinforced biocomposite implants, the inherent material properties of the biocomposite (i.e. the biocomposite in amorphous or non-aligned form) are actually quite low and can approximate the mechanical properties of the polymer alone. As such, implant geometries for implants constructed from these biocomposite materials does not inherently determine implants that are mechanically strong or stiff.

However, the medical implants of the present invention in at least some embodiments are able to exceed the mechanical properties of previous bioabsorbable implants, including previous biocomposite implants in one or more mechanical axes and in one or more mechanical parameters. Preferably these implants feature structures and forms in which the reinforcing fibers are aligned within the implant in order to provide the implant load bearing strength and stiffness in the axes in which these properties are biomechanically required. Thus, either the entire implant or segments of the implant are anisotropic (i.e. they have different mechanical properties in different axes). With these anisotropic implants, the implant mechanical design cannot rely solely on the geometry of each part. Rather, the specific alignment of the reinforcing fibers within the implant and the resulting anisotropic mechanical profile are a key parameter in determining the biomechanical function of the implant.

Aside from the mechanical considerations related to the anisotropic medical implants, there are additional limitations in that medical implants using these reinforced biocomposite materials cannot be designed according to existing implant designs due to the limitations associated with producing parts from these composite materials.

For example, metal implants or permanent polymer implants may be produced by machining. Even fiber-reinforced permanent polymer implants may be machined without adversely affecting the mechanical properties. However, absorbable, reinforced composite material implants cannot be machined without causing damage to the underlying material since machining will expose reinforcing fibers from the polymer, thus causing their strength to degrade quickly once they are directly exposed to body fluid following implantation.

At the other end of the spectrum, pure polymer or very short (<4 mm) fiber-reinforced polymer implants may be manufactured using straightforward injection molding processes. Injection molding of these materials does not, however, result in sufficiently strong implants. Therefore, specialized designs and production methods are required in order to design and produce an implant that can benefit from the superior mechanical properties of the previously described reinforced bioabsorbable composite materials.

The term "biodegradable" as used herein also refers to materials that are degradable, resorbable or absorbable in the body.

The term "load bearing" optionally also includes partially load bearing. According to various embodiments, the load bearing nature of the device (implant) may optionally include flexural strengths above 200 MPa, preferably above 300 MPa, more preferably above 400 MPa, 500 MPa, and most preferably above 600 MPa or any integral value in between.

Unless otherwise defined, all technical and scientific terms used herein have the same meaning as commonly understood by one of ordinary skill in the art to which this invention belongs. The materials, methods, and examples provided herein are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3A shows a sample with majority of layers with fiber orientation perpendicular to implant longitudinal axis. FIG. 3B shows a sample with majority of layers with fiber orientation parallel to implant longitudinal axis;

FIG. 5A shows an amorphous fiber orientation sample; FIG. 5B shows a sample with majority of layers with fiber orientation perpendicular to implant longitudinal axis. FIG. 5C shows a sample with majority of layers with fiber orientation parallel to implant longitudinal axis;

FIG. 8A is a photo of the pin along its length; FIG. 8B is a photo of the cross-section of the pin;

FIG. 9A is a photo of the pin along its length; FIG. 9B is a photo of the cross-section of the pin.

FIGS. 10A, 10B, 10C show the decrease in mechanical properties due to incubation under conditions that force degradation; FIG. 11A shows force distribution on a hollow cylinder pin implant with a wall thickness made of 5 layers as demonstrated in FIG. 11B.

DETAILED DESCRIPTION OF SOME EMBODIMENTS

Figure 1C:
FIGS. 1A, 1B, 1C show some exemplary plates according to at least some embodiments of the present invention.

A medical implant according to at least some embodiments of the present invention is suitable for load-bearing orthopedic implant applications and comprises one or more bioabsorbable materials where sustained mechanical strength and stiffness are critical for proper implant function.

According to at least some embodiments of the present invention, there is provided orthopedic implants, such as those for bone fixation, made from reinforced bioabsorbable composite materials. Specifically, implants according to at least some embodiments incorporate characteristics, features, or properties that can either only be achieved using the reinforced bioabsorbable composite materials or are specifically advantageous for implants comprised of these types of materials, or optionally a combination of both in a single implant.

Without wishing to be limited by a closed list, the material-specific design benefits are optionally provided by one or more of the following unique characteristics of implants manufactured from this material:

1. Absorbable structural implants wherein strength and stiffness properties are anisotropic. The bending resistance and other mechanical properties of these implants depends greatly on the specific design of the part and of the alignment of reinforcing fibers within the part. It is therefore possible to design such implants efficiently such that they provide sufficient support in the necessary axes (for example, flexural stiffness) without comprising an excessive amount of material that would provide equivalent support in the remaining axes (for example, tensile stiffness).

2. Low profile/minimally invasive/material efficient design for absorbable implant that take advantage of the strength and stiffness characteristics of the reinforced absorbable composite material to create implants that achieve bone fixation with minimal profile. By "minimal profile", it is meant that the implant is reduced in size in at least one dimension in comparison with an equivalent currently available implant that is not made from such composite material.

3. Load bearing absorbable bone implants, as opposed to previous absorbable implants which did not approach the stiffness of cortical bone.

4. Small functional features, such as anchors, ridges, teeth, etc that require the reinforcement in order to be strong enough to be functional. Previous absorbable materials may not have had sufficient strength for such features.

5. The capability of being produced according to fiber-reinforced composite specific manufacturing techniques such as compression molding, pultrusion, etc.

6. Reduced damage to surrounding tissues, including both soft tissues and bone tissues, as compared with the trauma of stress risers or stress shielding that can arise from use of high modulus (such as metal) implants.

The present invention, according to at least some embodiments, thus provides medical implants that are useful as structural fixation for load-bearing purposes, exhibiting sustained mechanical properties.

The present invention, according to at least some embodiments, further comprises a biodegradable composite material in which the drawbacks of the prior art materials can be minimized or even eliminated, i.e. the composite retains its strength and modulus in vivo for a time period sufficient for bone healing for example. Mechanical strength as used here includes, but is not limited to, bending strength, torsion strength, impact strength, compressive strength and tensile strength.

The presently claimed invention, in at least some embodiments, relate to a biocomposite material comprising a biocompatible polymer and a plurality of reinforcing fibers, wherein said reinforcing fibers are oriented in a parallel orientation.

The biocomposite material has one or more mechanical properties which feature an increased extent or degree as compared to such a material with reinforcing fibers oriented in a non-parallel orientation. Optionally such a non-parallel orientation is a perpendicular or amorphous (non-oriented) orientation, elastic modulus, tensile modulus, compression modulus, shear modulus, bending moment, moment of inertia, bending strength, torsion strength, shear strength, impact strength, compressive strength and/or tensile strength. The increased extent or degree may optionally be at least twice as great, at least five times as great, at least ten times as great, at least twenty times as great, at least fifty times as great, or at least a hundred times as much, or any integral value in between.

Optionally the mechanical properties can comprise any one of Flexural strength, Elastic modulus and Maximum load, any pair of same or all of them. Optionally density and/or volume are unchanged or are similar within 5%, within 10%, within 15%, within 20%, any integral value in between or any integral value up to 50%.

Optionally the biocomposite implant as described herein is swellable, having at least 0.5% swellability, at least 1%, 2% swellability, and less than 20% swellability, preferably less than 10% or any integral value in between.

Optionally, the swellability in one mechanical axis is greater than the swellability in a second mechanical axis. Preferably the difference in swelling percentage (%) between axes is at least 10%, at least 25%, at least 50%, or at least 100%, or any integral value in between.

After exposure to biological conditions for 1 hour, 12 hours, 24 hours, 48 hours, five days, one week, one month, two months or six months or any time value in between, the biocomposite material implants preferably retain at least 10%, at least 20%, at least 50%, at least 60%, at least 75%, at least 85% or up to 100% of flexural strength, Modulus and/or Max load, and/or volume, or any integral value in between. By "biological conditions" it is meant that the temperature is between 30-40 C but preferably is at 37 C. Optionally, fluid conditions replicate those in the body as well, under "simulated body fluid" conditions.

The flexural strength of the implant or segment of the implant is preferably at least 200 MPA, at least 400 mPa, at least 600 mPA, at least 1000 mPA or any integral value in between.

Relevant implants may include bone fixation plates, intramedullary nails, joint (hip, knee, elbow) implants, spine implants, and other devices for such applications such as for fracture fixation, tendon reattachment, spinal fixation, and spinal cages.

According to at least some embodiments, there are provided medical implants for bone or soft tissue fixation comprising a biodegradable composite, wherein said composite optionally and preferably has the following properties:

(i) wherein biodegradable composite comprises one or more biodegradable polymers and a resorbable, reinforcement fiber; and (ii) wherein one or more segments comprising the medical implant have a maximum flexural modulus in the range of 6 GPa to 30 GPa and flexural strength in the range of 100 MPa to 1000 MPa; and (iii) wherein the average density of the composite is in the range of 1.1-3.0 g/cm$^3$.

Preferably, average density of the composite is in the range of 1.2-2.0 g/cm$^3$.

More preferably, average density of the composite is in the range of 1.3-1.6 g/cm$^3$.

Preferably, flexural modulus is in the range of 10 GPa to 28 GPa and more preferably in the range of 15 to 25 GPa.

Preferably, flexural strength is in the range of 200-800 MPa. More preferably, 400-800 MPa.

In a preferred embodiment of the present invention, at least 50% of elastic modulus is retained following exposure to simulated body fluid (SBF) at 50° C. for 3 days. More preferably at least 70% is retained, and even more preferably at least 80% is retained.

In a preferred embodiment of the present invention, at least 20% of strength is retained following exposure to simulated body fluid (SBF) at 50° C. for 3 days. More preferably at least 30% is retained, and even more preferably at least 40% is retained.

In a preferred embodiment of the present invention, at least 50% of elastic modulus is retained following exposure to simulated body fluid (SBF) at 37° C. for 3 days. More preferably at least 70%, and even more preferably at least 85%.

In a preferred embodiment of the present invention, at least 30% of strength is retained following exposure to simulated body fluid (SBF) at 37° C. for 3 days. More preferably at least 45%, and even more preferably at least 60%.

Specifically regarding medical implants described herein that contain one or more segments that can be anisotropic, this anisotropicity reflects a significant divergence from what has be previously accepted in medical, and specifically orthopedic, implants in that the anisotropic structure results in implants in which there are mechanical properties in one or more axis that are less than the optimal mechanical properties which may be achieved by the materials from which the implant is comprised. In contrast, traditional implants have relied upon the uniform mechanical properties of the materials from which they are comprised as this does not require compromising in any axis.

The anisotropic approach can only be applied following biomechanical analysis to determine that greater implant mechanical properties is required in certain axes as opposed to other axes. For example, an implant may be subjected to very high bending forces but only nominal tensile forces and therefore require a much greater emphasis on bending forces. Other relevant axes of force in a medical implant can include tensile, compression, bending, torsion, shear, pull-out (from bone) force, etc.

There are several factors that affect the mechanical properties of an implant. As described above, material composition alone results in a generally uniform or isotropic structure. Without wishing to be limited by a closed list or a single hypothesis, within fiber-reinforced biocomposite medical implants, an anisotropic structure may result from one or more of the following characteristics:

1. The weight ratio of reinforcing fibers to biopolymer. Preferably this ratio is in the range of 1:1 to 3:1 and more preferably 1.5:1 to 2.5:1.

2. The density of the medical implant (this characteristic is also determined to some extent the ratio of reinforcing fiber to polymer)
3. The diameter of reinforcing fiber. The average fiber diameter is preferably between 5 and 50 μm. More preferably between 10-30 μm.
4. Length of fiber (continuous fiber, long fiber, short fiber). Preferably, having continuous fiber reinforcement with fibers that run across the entire implant.
5. The alignment of fibers or fiber layers. Preferably, in each segment of the implant, a majority of fibers or fiber layers are aligned or partially aligned with the axis that will be exposed to the highest bending forces. If partially aligned, then preferably within a 45 angle of the axis.
6. The number of fibers or fiber layers aligned in any given direction. Preferably fiber layers are 0.1 to 1 mm in thickness and more preferably 0.15 to 0.25 mm.
7. The order of fiber layers.

In one embodiment of the present invention, the medical implant is a pin, screw, or wire.

Preferably, a pin or wire of 2 mm external diameter will have a shear load carrying capacity of greater than 200 N. More preferably shear load carrying capacity of 2 mm pin will exceed 400 N and most preferably will exceed 600 N.

Bioabsorbable Polymers

In a preferred embodiment of the present invention, the biodegradable composite comprises a bioabsorbable polymer.

The medical implant described herein may be made from any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin. Examples of suitable biodegradable polymers include, but are not limited to polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones) e.g., 1,4-dioxepan-2-one and 1,5-dioxepan-2-one), ethylene glycol, ethylene oxide, esteramides, γ-ydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate, (polyurethanes, polyanhydrides, polymer drugs (e.g., polydiflunisol, polyaspirin, and protein therapeutics (and copolymers and combinations thereof. Suitable natural biodegradable polymers include those made from collagen, chitin, chitosan, cellulose, poly (amino acids), polysaccharides, hyaluronic acid, gut, copolymers and derivatives and combinations thereof.

According to the present invention, the biodegradable polymer may be a copolymer or terpolymer, for example: polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically-3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-ε-capralactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly(ester anhydrides); and mixtures thereof; and natural polymers, such as sugars; starch, cellulose and cellulose derivatives, polysaccharides, collagen, chitosan, fibrin, hyaluronic acid, polypeptides and proteins. Mixtures of any of the above-mentioned polymers and their various forms may also be used.

The biodegradable composite is preferably embodied in a polymer matrix, which may optionally comprise any of the above polymers. Optionally and preferably, it may comprise a polymer selected from the group consisting of a bioabsorbable polyester, PLLA (poly-L-lactide), PDLLA (poly-DL-lactide), PLDLA, PGA (poly-glycolic acid), PLGA (poly-lactide-glycolic acid), PCL (Polycaprolactone), PLLA-PCL and a combination thereof. If PLLA is used, the matrix preferably comprises at least 30% PLLA, more preferably 50%, and most preferably at least 70% PLLA. If PDLA is used, the matrix preferably comprises at least 5% PDLA, more preferably at least 10%, most preferably at least 20% PDLA.

Optionally, the inherent viscosity (IV) of the polymer matrix (independent of the reinforcement fiber) is in the range of 0.2-6 dl/g, preferably 1.0 to 3.0 dl/g, more preferably in the range of 1.5 to 2.4 dl/g, and most preferably in the range of 1.6 to 2.0 dl/g.

Inherent Viscosity (IV) is a viscometric method for measuring molecular size. IV is based on the flow time of a polymer solution through a narrow capillary relative to the flow time of the pure solvent through the capillary.

Reinforced Biocomposite

According to at least some embodiments of the present invention, the medical implant comprises a reinforced biocomposite (i.e. a bioabsorbable composite that includes the previously described polymer and also incorporates a reinforcing filler, generally in fiber form, to increase the mechanical strength of the polymer). For the avoidance of doubt, the terms "filler" and "fiber" are used interchangeably to describe the reinforcing material structure.

In a more preferred embodiment of the present invention, the reinforced bioabsorbable polymer is a reinforced polymer composition comprised of any of the above-mentioned bioabsorbable polymers and a reinforcing filler, preferably in fiber form. The reinforcing filler may be comprised of organic or inorganic (that is, natural or synthetic) material. Reinforcing filler may be a biodegradable glass or glass-like materials, a ceramic, a mineral composition (optionally including one or more of hydroxyapatite, tricalcium phosphate, calcium sulfate, calcium phosphate), a cellulosic material, a nano-diamond, or any other filler known in the art to increase the mechanical properties of a bioabsorbable polymer. The filler may also optionally be a fiber of a bioabsorbable polymer itself. Preferably, reinforcing fiber is comprised of a bioabsorbable glass, ceramic, or mineral composition.

Preferably, reinforcement fiber is comprised of silica-based mineral compound such that reinforcement fiber comprises a bioresorable glass fiber, which can also be termed a bioglass fiber composite.

According to at least some embodiments, bioresorbable glass fiber may optionally have oxide compositions in the following mol. % ranges (as a percent over the glass fiber composition):
$Na_2O$: 11.0-19.0 mol. %
$CaO$: 9.0-14.0 mol. %
$MgO$: 1.5-8.0 mol. %
$B_2O_3$: 0.5-3.0 mol. %
$Al_2O_3$: 0-0.8 mol. %
$P_2O_3$: 0.1-0.8 mol. %
$SiO_2$: 67-73 mol. %
but preferably in the following mol. % ranges:
$Na_2O$: 12.0-13.0 mol. %
$CaO$: 9.0-10.0 mol. %
$MgO$: 7.0-8.0 mol. %
$B_2O_3$: 1.4-2.0 mol. %
$P_2O_3$: 0.5-0.8 mol. %
$SiO_2$: 68-70 mol. %

Additional optional bioresorable glass compositions are described in the following patent applications, which are hereby incorporated by reference as if fully set forth herein: Biocompatible composite and its use (WO2010122098); and Resorbable and biocompatible fibre glass compositions and their uses (WO2010122019).

Tensile strength of the reinforcement fiber is preferably in the range of 1200-2800 MPa, more preferably in the range of 1600-2400 MPa, and most preferably in the range of 1800-2200 MPa.

Elastic modulus of the reinforcement fiber is preferably in the range of 30-100 GPa, more preferably in the range of 50-80 GPa, and most preferably in the range of 60-70 GPa.

Reinforcing filler is preferably incorporated in the bioabsorbable polymer matrix of the biocomposite in fiber form. Preferably, such fibers are continuous fibers.

Preferably continuous fibers are aligned within the implant such that the ends of fibers don't open at the surface of the implant.

Preferably, fibers are distributed evenly within the implant.

Specifically within bioabsorbable fiber-reinforced composites, achieving the high strengths and stiffness required for many medical implant applications can require the use of continuous-fiber reinforcement rather than short or long fiber reinforcement. This creates a significant difference from the implant structures, architectures, designs, and production techniques that have been previously used with medical implants produced from polymers or composites comprising short or long fiber reinforced polymers. Those implants are most commonly produced using injection molding, or occasionally 3-D printing, production techniques. The production of these implants generally involves homogeneity of the material throughout the implant and the finished implant is then comprised of predominantly isotropic material. However, with continuous fiber-reinforcement, the fibers must be carefully aligned such that each fiber or bundle of fibers runs along a path within the composite material such that they will provide reinforcement along specific axes within the implant to provide stress resistance where it is most needed.

The present invention provides, in at least some embodiments, implant compositions from continuous-fiber reinforced bioabsorbable composite materials that are a significant step forward from previous bioabsorbable implants in that they can achieve sustainably high, load bearing strengths and stiffness. Additionally, many embodiments of the present invention additionally facilitate these high strength levels with efficient implants of low volume since the anisotropic nature of the implants can allow the implants to achieve high mechanical properties in axes where those properties are needed (for example in bending resistance) without necessitating the additional volume that would be needed to uniformly provide high mechanical properties in all other axes.

According to at least some embodiments, there is provided a medical implant comprising a plurality of composite layers, said layers comprising a biodegradable polymer and a plurality of uni-directionally aligned continuous reinforcement fibers. Optionally and preferably, the biodegradable polymer is embodied in a biodegradable composite. Also optionally and preferably, the fibers are embedded in a polymer matrix comprising one or more bioabsorbable polymers.

According to at least some embodiments, the composite layers are each comprised of one or more composite tapes, said tape comprising a biodegradable polymer and a plurality of uni-directionally aligned continuous reinforcement fibers. Optionally and preferably, the biodegradable polymer is embodied in a biodegradable composite. Also optionally and preferably, the fibers are embedded in a polymer matrix comprising one or more bioabsorbable polymers.

Preferably, the composite tape layer comprises reinforcement fibers that are pre-impregnated with polymer.

Preferably, each composite layer is of thickness 0.05 mm-0.5 mm, more preferably 0.15-0.35 mm, and most preferably 0.1-0.25 mm.

Preferably, each composite tape is of width 2-30 mm, more preferably tape is of width 4-16 mm, and most preferably of width 6-12 mm.

Preferably, reinforcement fiber content within the composite tape is in the range of 20-70%, more preferably in the range of 30-60%, more preferably in the range of 40-50%, and most preferably 45-50% over the entire composite tape materials.

Optionally and preferably, the fiber-reinforced biodegradable composite within the implant has a flexural modulus exceeding 10 GPa and flexural strength exceeding 100 MPa.

Optionally, the fiber-reinforced biodegradable composite within the implant has flexural strength in range of 200-1000 MPa, preferably 300-800 MPa, more preferably in the range of 400-800 MPa, and most preferably in the range of 500-800 MPa Optionally, the fiber-reinforced biodegradable composite within the implant has elastic modulus in range of 10-30 GPa, preferably 12-28 GPa, more preferably in the range of 16-28 GPa, and most preferably in the range of 20-26 GPa.

Optionally, fibers may be aligned at an angle to the longitudinal axis (i.e. on a diagonal) such that the length of the fiber may be greater than 100% of the length of the implant. Optionally and preferably, a majority of reinforcement fibers are aligned at an angle that is less than 90°, alternatively less than 60°, or optionally less than 45 from the longitudinal axis.

Preferably, the implant preferably comprises between 2-20 composite tape layers, more preferably between 2-10 layers, and most preferably between 2-6 layers; wherein each layer may be aligned in a different direction or some of the layers may be aligned in the same direction as the other layers.

Preferably, the maximum angle between fibers in at least some of the layers is greater than the angle between the fibers in each layer and the longitudinal axis. For example, one layer of reinforcing fibers may be aligned and a right diagonal to the longitudinal axis while another layer may be aligned at a left diagonal to the longitudinal axis.

Optionally and preferably, the composite composition additionally includes a compatibilizer, which for example be such an agent as described in WO2010122098, hereby incorporated by reference as if fully set forth herein.

Reinforcing fiber diameter preferably in range of 2-40 um, preferably 8-20 um, most preferably 12-18 um (microns).

Preferably, the implant includes only one composition of reinforcing fiber.

Preferably fibers don't open at the surface of the implant.

Numerous examples of reinforced polymer compositions have previously been documented. For example: A biocompatible and resorbable melt derived glass composition where glass fibers can be embedded in a continuous polymer matrix (EP 2 243 749 A1), Biodegradable composite comprising a biodegradable polymer and 20-70 vol % glass fibers (WO2010128039 A1), Resorbable and biocompatible fiber glass that can be embedded in polymer matrix (US 2012/0040002 A1), Biocompatible composite and its use (US 2012/0040015 A1), Absorbable polymer containing poly[succinimide] as a filler (EP0 671 177 B1).

In a more preferred embodiment of the present invention, the reinforcing filler is covalently bound to the bioabsorbable polymer such that the reinforcing effect is maintained for an extended period. Such an approach has been described in US 2012/0040002 A1 and EP 2243500B1, hereby incorporated by reference as if fully forth herein, which discusses a composite material comprising biocompatible glass, a biocompatible matrix polymer and a coupling agent capable of forming covalent bonds.

Fabrication of the Implant

Any of the above-described bioabsorbable polymers or reinforced bioabsorbable polymers may be fabricated into any desired physical form for use with the present invention. The polymeric substrate may be fabricated for example, by compression molding, casting, injection molding, pultrusion, extrusion, filament winding, composite flow molding (CFM), machining, or any other fabrication technique known to those skilled in the art. The polymer may be made into any shape, such as, for example, a plate, screw, nail, fiber, sheet, rod, staple, clip, needle, tube, foam, or any other configuration suitable for a medical device.

Load-Bearing Mechanical Strength

The present invention particularly relates to bioabsorbable composite materials that can be used in medical applications that require high strength and a stiffness compared to the stiffness of bone. These medical applications require the medical implant to bear all or part of the load applied by or to the body and can therefore be referred to generally as "load-bearing" applications. These include bone fixation, fracture fixation, tendon reattachment, joint replacement, spinal fixation, and spinal cages.

The flexural strength preferred from a bioabsorbable composite (such as a reinforced bioabsorbable polymer) for use in the load-bearing medical implant is at least 200 MPa, preferably above 400 MPa, more preferably above 600 MPa, and even more preferably above 800 MPa. The Elastic Modulus (or Young's Modulus) of the bioabsorbable composite for use with present invention is preferably at least 10 GPa, more preferably above 15 GPa, and even more preferably above 20 GPa but not exceeding 100 GPa and preferably not exceeding 60 GPa.

Sustained Mechanical Strength

There is a need for the bioabsorbable load-bearing medical implants of the present invention to maintain their mechanical properties (high strength and stiffness) for an extended period to allow for sufficient bone healing. The strength and stiffness preferably remains above the strength and stiffness of cortical bone, approximately 150-250 MPa and 15-25 GPa respectively, for a period of at least 3 months, preferably at least 6 months, and even more preferably for at least 9 months in vivo (i.e. in a physiological environment).

More preferably, the flexural strength remains above 400 MPa and even more preferably remains above 600 MPa.

The present invention overcomes the limitations of previous approaches and provides medical implants comprised of biodegradable compositions that retain their high mechanical strength and stiffness for an extended period sufficient to fully support bone regeneration and rehabilitation.

"Biodegradable" as used herein is a generalized term that includes materials, for example polymers, which break down due to degradation with dispersion in vivo. The decrease in mass of the biodegradable material within the body may be the result of a passive process, which is catalyzed by the physicochemical conditions (e.g. humidity, pH value) within the host tissue. In a preferred embodiment of biodegradable, the decrease in mass of the biodegradable material within the body may also be eliminated through natural pathways either because of simple filtration of degradation by-products or after the material's metabolism ("Bioresorption" or "Bioabsorption"). In either case, the decrease in mass may result in a partial or total elimination of the initial foreign material. In a preferred embodiment, said biodegradable composite comprises a biodegradable polymer that undergoes a chain cleavage due to macromolecular degradation in an aqueous environment.

A polymer is "absorbable" as described herein if it is capable of breaking down into small, non-toxic segments which can be metabolized or eliminated from the body without harm. Generally, absorbable polymers swell, hydrolyze, and degrade upon exposure to bodily tissue, resulting in a significant weight loss. The hydrolysis reaction may be enzymatically catalyzed in some cases. Complete bioabsorption, i.e. complete weight loss, may take some time, although preferably complete bioabsorption occurs within 24 months, most preferably within 12 months.

The term "polymer degradation" means a decrease in the molecular weight of the respective polymer. With respect to the polymers, which are preferably used within the scope of the present invention said degradation is induced by free water due to the cleavage of ester bonds. The degradation of the polymers as for example used in the biomaterial as described in the examples follows the principle of bulk erosion. Thereby a continuous decrease in molecular weight precedes a highly pronounced mass loss. Such loss of mass is attributed to the solubility of the degradation products. Methods for determination of water induced polymer degradation are well known in the art such as titration of the degradation products, viscometry, differential scanning calorimetry (DSC).

Bulk degradation refers to a process of degradation in which there is at least some perfusion of fluid through the material that is being degraded, such as the body of the implant, thereby potentially degrading the bulk of the material of the implant (as opposed to the external surface alone). This process has many effects. Without wishing to be limited to a closed list, such bulk degradation means that simply making an implant larger or thicker may not result in improved retained strength.

Surface degradation refers to a process of degradation in which the external surface undergoes degradation. However, if there is little or no perfusion of fluid through the material that is being degraded, then the portion of the implant that is not on the surface is expected to have improved retained strength over implants in which such perfusion occurs or occurs more extensively.

Clinical Applications

The medical implants discussed herein are generally used for bone fracture reduction and fixation to restore anatomical relationships. Such fixation optionally and preferably includes one or more, and more preferably all, of stable fixation, preservation of blood supply to the bone and surrounding soft tissue, and early, active mobilization of the part and patient.

There are several exemplary, illustrative, non-limiting types of bone fixation implants for which the materials and concepts described according to at least some embodiments of the present invention may be relevant, as follows:

Screws

Screws are used for internal bone fixation and there are different designs based on the type of fracture and how the screw will be used. Screws come in different sizes for use with bones of different sizes. Screws can be used alone to hold a fracture, as well as with plates, rods, or nails. After the bone heals, screws may be either left in place or removed.

Screws are threaded, though threading can be either complete or partial. Screws can include compression screws, locking screws, and/or cannulated screws. External screw diameter can be as small as 0.5 or 1.0 mm but is generally less than 3.0 mm for smaller bone fixation. Larger bone cortical screws can be up to 5.0 mm and cancellous screws can even reach 7-8 mm. Some screws are self-tapping and others require drilling prior to insertion of the screw. For cannulated screws, a hollow section in the middle is generally larger than 1 mm diameter in order to accommodate guide wires.

Wires/Pins

Wires are often used to pin bones back together. They are often used to hold together pieces of bone that are too small to be fixed with screws. They can be used in conjunction with other forms of internal fixation, but they can be used alone to treat fractures of small bones, such as those found in the hand or foot. Wires or pins may have sharp points on either one side or both sides for insertion or drilling into the bone.

"K-wire" is a particular type of wire generally made from stainless steel, titanium, or nitinol and of dimensions in the range of 0.5-2.0 mm diameter and 2-25 cm length. "Steinman pins" are general in the range of 2.0-5.0 mm diameter and 2-25 cm length. Nonetheless, the terms pin and wire for bone fixation are used herein interchangeably.

Anchors

Anchors and particularly suture anchors are fixation devices for fixing tendons and ligaments to bone. They are comprised of an anchor mechanism, which is inserted into the bone, and one or more eyelets, holes or loops in the anchor through which the suture passes. This links the anchor to the suture. The anchor which is inserted into the bone may be a screw mechanism or an interference mechanism. Anchors are generally in the range of 1.0-6.5 mm diameter Cable, Ties, Wire Ties Cables, ties, or wire ties (one example of wire tie is Synthes ZipFix™) can be used to perform fixation by cerclage, or binding, bones together. Such implants may optionally hold together bone that cannot be fixated using penetration screws or wires/pin, either due to bone damage or presence of implant shaft within bone. Generally, diameter of such cable or tie implants is optionally in the range of 1.0 mm-2.0 mm and preferably in the range of 1.25-1.75 mm. Wire tie width may optionally be in the range of 1-10 mm.

Nails or Rods

In some fractures of the long bones, medical best practice to hold the bone pieces together is through insertion of a rod or nail through the hollow center of the bone that normally contains some marrow. Screws at each end of the rod are used to keep the fracture from shortening or rotating, and also hold the rod in place until the fracture has healed. Rods and screws may be left in the bone after healing is complete. Nails or rods for bone fixation are generally 20-50 cm in length and 5-20 mm in diameter (preferably 9-16 mm). A hollow section in the middle of nail or rod is generally larger than 1 mm diameter in order to accommodate guide wires.

Other non-limiting, illustrative examples of bone fixation implants may optionally include plates, plate and screw systems, and external fixators.

Any of the above-described bone fixation implants may optionally be used to fixate various fracture types including but not limited to comminuted fractures, segmental fractures, non-union fractures, fractures with bone loss, proximal and distal fractures, diaphyseal fractures, osteotomy sites, etc.

Bending Resistance

The primary mechanical challenge to wires or pins used for bone fixation is providing mechanical support (i.e. bending resistance) under bending/flexural stress to prevent the stress from creating a gap between the bone surfaces in the fracture which can prevent good bone healing. For absorbable bone fixation implants, it is desirable for the implant to provide bending resistance such that the implant deflects a similar amount or less than the bones which it is fixating when exposed to bending stress. It is further desirable for the implant to provide this bending resistance with the minimal profile (i.e. minimal amount of material) in order to minimize the amount of degradation products over time and also to reduce implant cost.

For a wire or pin, the amount of deflection it undergoes when subjected to a flexural stress is directly related to (i) the flexural modulus of the material of which the implant is made; and (ii) the second moment of inertia of the cross-section of the wire or pin across the axis across which the flexural stress is being applied.

Second moment of inertia refers to the property of a shape that directly correlates to its ability to resist bending and deflection. Second moment of inertia can alternatively be referred to as second moment of area, moment of inertia of plane area, area moment of inertia, polar moment of area or second area moment.

In a preferred embodiment of the present invention, the elastic modulus of the implant or a segment of the implant as measured with flexural/bending testing is greater than the elastic modulus of the implant or a segment of the implant as measured with tensile testing. Preferably, the difference is greater than 5%, more preferred the difference is greater than 10%, even more preferred greater than 20%, 30%, 40%, 50%.

In a preferred embodiment of the present invention, the flexural/bending strength of the implant is greater than its tensile or compressive strength. In a more preferred embodiment, this difference is greater than 5%. Even more preferred, the higher flexural/bending strength as compared with tensile or compressive strength is greater by at least 10%, 30%, 50%, 70%, and most preferably 100%.

In an optional embodiment, the anisotropic nature of the medical implants described according to at least some embodiments of the present invention result in the mechanical properties in the bending axis that are superior to the mechanical properties in the tensile or compressive axis. This difference can be at least partially determined by the alignment, orientation, or structure of reinforcing fibers with the bioabsorbable polymer matrix, as described in more detail above.

In a hollow tube geometry, its flexural/bending stiffness is relatively greater than its tensile stiffness. The flexural stiffness is relative to the second moment of inertia around the axis of bending, for example the second moment of inertia around the midline axis of a square pin/beam is $Ix=bh3/12$ and for a hollow circular pin/beam, $Ix=\pi(do4-di4)/64$. Conversely, the tensile stiffness is relative to the cross-sectional area, $A=bh$ for a square pin/beam and $A=\pi(do2-di2)/4$ for a hollow circular pin/beam.

In a preferred embodiment of the present invention, one or more voids are present within the implant, such that the second moment of inertia of the cross-section of the wire or pin across the mid-line axis of the implant is less than the second moment of inertia for such a part with the same or similar external dimensions but a void-less (i.e. whole or solid) cross-sectional area. Preferably, the reduction in the second moment of inertia is smaller than 30%, more preferably 20% and most preferably 10% than for a solid part.

Alternatively, a wire or pin may comprise open space between different struts, ribs, arms, etc of the wire or pin such that wire or pin forms an asterisk type cross-section thereby similarly providing increased relative flexural stiffness in relation to its tensile stiffness.

Preferably, the average cross-sectional area of the wire or pin is reduced by a greater percentage than the average second moment of inertia of its cross-section as compared to a solid part with similar dimensions as previously described. More preferably, the cross-sectional area is more than 20% smaller while the second moment of inertia is reduced by less than 20%. Even more preferably, the cross-sectional area is more than 20% smaller while the second moment of inertia is reduced by less than 10%.

Dimensions

For orthopedic implants, it is desirable for the implant to have a minimal profile so as to allow for implantation with minimal soft tissue damage. Furthermore, it is preferable to produce the implant with sufficient robustness to provide necessary mechanical strength but otherwise not contain extraneous material.

In a preferred embodiment of the present invention, the external diameter of the wire or pin is less than 15 mm, more preferably less than 10 mm, even more preferably less than 5 mm and most preferably less than 3 mm.

In a preferred embodiment of the present invention, the wall thickness of the wire or pin is less than 5 mm, more preferably less than 3 mm, even more preferably less than 1 mm and most preferably less than 0.7 mm.

Voids in Implant

As described above, it may be desirable to have a wire or pin that is hollow in order to provide bending resistance with the most efficient amount of material. Nonetheless, there are potential complications involved in implanting a hollow implant in bone, as non-bone tissue cells, such as fibroblasts, can penetrate into the hollow void and thereby impede or slow regeneration of bone in that area.

In a preferred embodiment of the present invention, the wire or pin contains a hollow section or void internally but such void is covered such that cells cannot invade void prior to degradation of implant material.

In another embodiment of the present invention, the hollow section can be filled with active ingredients such as antibiotics, growth factors or bone filler to prevent such invasion.

In another embodiment hollow section can be used to introduce active ingredients into fracture area via holes in the wall of the hollow wire or pin.

Example #1

The below example describes the extent to which the anisotropic nature of the herein described reinforced bio-composite implants impacts the mechanical properties of the implants. Depending on the mechanical property parameter, the differences in the degree of anisotropicity in a medical implant or medical implant part can reach even 5× or greater. Without wishing to be limited by a single hypothesis, these differences may be due to differences between alignments of reinforcing fibers within the implant.

Materials and Methods

Rectangular testing samples (dimensions 50.8 mm×12.7 mm×1 mm), simulating plates used for small bone fixation, were produced using reinforced composite material. Material composite was comprised of PLDLA 70/30 polymer reinforced with 40%-50% w/w continuous mineral fibers. Mineral fibers were as described for composition "NX-8" in Lehtonen T J et al. *Acta Biomaterialia* 9 (2013) 4868-4877. Mineral composition was specifically approximately Na2O 14%, MgO 5.4%, CaO 9%, B2O3 2.3%, P2O5 1.5%, and SiO2 67.8% w/w. All testing samples were from one plate, manufactured by compression molding of five layers of composite material, each comprised of the PLDLA polymer with embedded uni-directionally aligned continuous fibers. Each layer was 0.18 mm thick.

In four samples, orientation of layers relative to longitudinal axis of implant were 0° (parallel to implant longitudinal axis), 45°, 0°, −45°, 0°. In four other samples, orientation of layers relative to longitudinal axis were 90° (perpendicular to implant longitudinal axis), −45°, 90°, 45°, 90°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.092 mm/min. Dimensions, weight and density of samples were measured. Statistical comparison between two treatments was performed using a t-test. A confidence level of $p=0.05$ was used.

Results

Figures 2A, 2B, 2C:
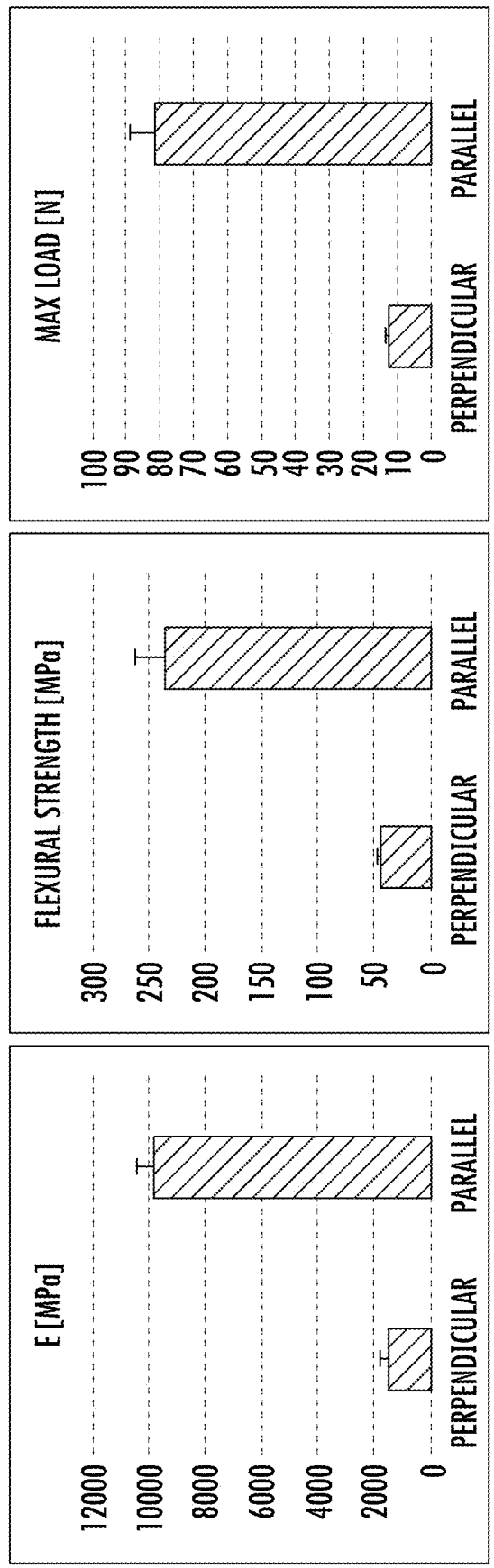
FIGS. 2A, 2B, 2C show the anisotropic properties of a bio-composite plate as demonstrated by the large difference in mechanical properties of samples with identical compositions, but with a majority of layers aligned at either 0° (Parallel) or 900 (Perpendicular) to the longitudinal axis of the implant sample (n=4)

FIG. 2 shows the anisotropic properties of a bio-composite plate as demonstrated by the large difference in mechanical properties of samples with identical compositions, but with a majority of layers aligned at either 0° (Parallel) or 90 (Perpendicular) to the longitudinal axis of the implant sample (n=4). The numerical results are summarized in Table 1.

TABLE 1

Mean values and standard deviations of statistically significant mechanical properties of the anisotropic implants. (n = 4). Density and Volume of the different samples were similar.

|  | E [MPa] | Flexural Strength [MPa] | Max Load [N] | Density [gr/ml] | Volume [mm$^3$] |
|---|---|---|---|---|---|
| Perpendicular | 1524.4 ± 281 | 45.9 ± 1.6 | 12.4 ± 1.4 | 1.48 ± 0.01 | 662.1 ± 32.3 |
| Parallel | 9795.4 ± 610 | 235.4 ± 25.4 | 81.4 ± 7.7 | 1.49 ± 0.03 | 694.0 ± 19.3 |
| Anisotropicity [%] [Par/perp*100] | 642.6 | 512.8 | 656.3 | | |

Figure 3A:
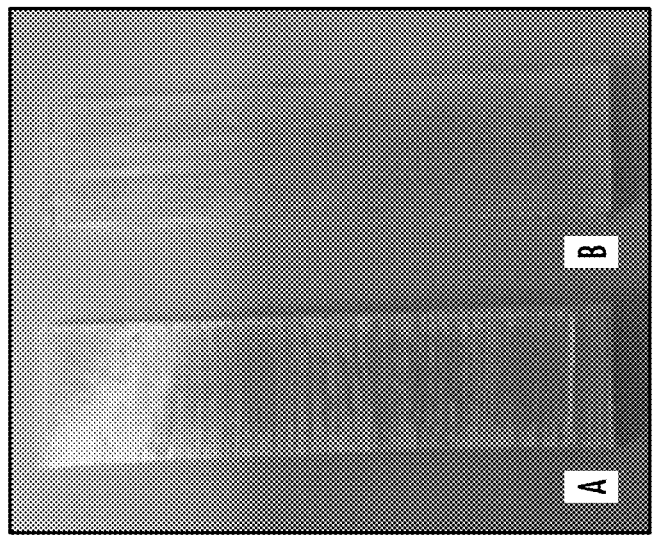
FIGS. 3A and 3B show representative examples of samples.
Figure 3B:
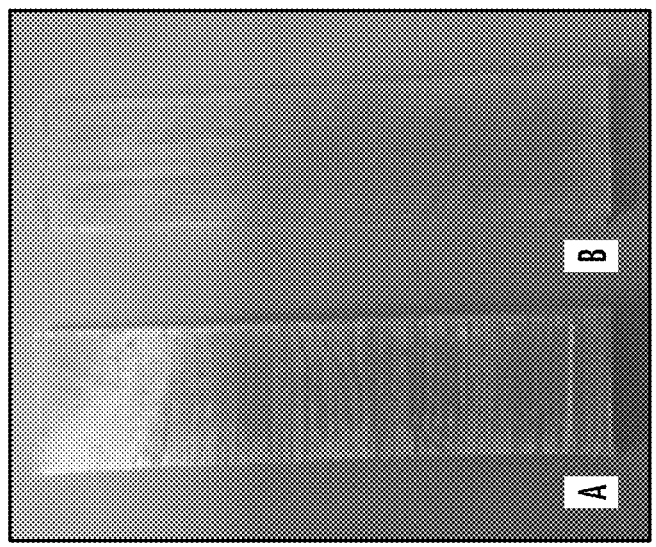

FIG. 3 shows representative examples of samples. FIG. 3A shows a sample with majority of layers with fiber orientation perpendicular to implant longitudinal axis. FIG. 3B shows a sample with majority of layers with fiber orientation parallel to implant longitudinal axis. The mechanical properties of sample B were superior to those of sample A. Anisotropicity of mechanical properties in this example was more than 500%. The anisotropocity was calculated as a percentage by dividing each of the mechanical parameter values as measured for the samples with perpendicular (tranverse) fiber alignment by the corresponding value as measured for the samples with parallel fiber alignment.

Example #2

The below example describes the extent to which the anisotropic nature of the herein described reinforced biocomposite implants impacts the mechanical properties of the implants. This example additionally shows that an implant comprised of a randomly distributed, or amorphous, composition of reinforced biocomposite materials will have far inferior mechanical properties in the desired axis to the herein described anisotropic medical implant with alignment of reinforcing fibers that maximizes the mechanical properties in the desired axis (in this case, bending force).

The example also demonstrates anisotropicity in that the modulus, when measured by flexural testing, can be either higher or lower than the tensile modulus of the same part depending on the directionality of the flexural test.

Materials and Methods

Rectangular testing samples (dimensions 50.8 mm×12.7 mm×0.7 mm), simulating plates used for small bone fixation, were produced using reinforced composite material. Material composite was as described in Example 1.

16 testing samples were produced, manufactured by compression molding of four layers of composite material. Each layer was 0.18 mm thick. In four samples, samples were each comprised of the PLDLA polymer with embedded uni-directionally aligned continuous fibers where orientation of layers relative to longitudinal axis of implant were 0° (parallel to implant longitudinal axis), 0°, 0°, 0°. In four other samples, orientation of layers relative to longitudinal axis were 90 (perpendicular to implant longitudinal axis), 90°, 90°, 90°. In four other samples, the continuous fiber embedded layers were not uni-directionally aligned but rather the layers were chopped into segments of approximately 3 mm and then molded together into the rectangular plates in bulk. In other words, the composition of these last four samples was identical to that of the continuous fiber groups but the material was used with random alignment, hereafter referred to as an "amorphous" form.

12 implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.47 mm/min (1.71 mm/min for amorphous plates due to thinner dimension). Dimensions, weight and density of samples were measured. 4 implant samples (n=4) were tested for tensile strength, tensile modulus and maximum load according to modified ASTM D3039M with 5 KN load cell and an appropriate fixture (220Q1125-95, TestResources, MN, USA). Sample span was 30 mm at the beginning of the test and cross head speed was set at 2 mm/min. Dimensions, weight and density of samples were recorded.

Results

Figures 4A, 4B, 4C:
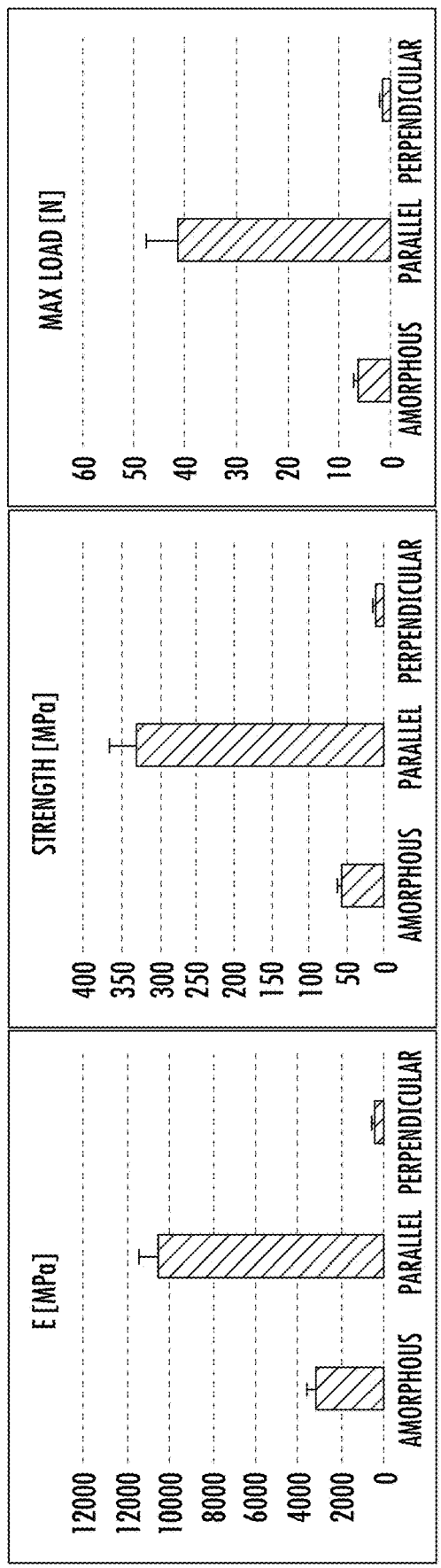
FIGS. 4A, 4B 4C show that the anisotropic properties of a bio-composite plate are directly affected by fiber orientation, as demonstrated by the large difference in mechanical properties of samples with identical compositions, but with non-aligned layers (Amorphous) or with layers aligned at either 0° (Parallel) or 90 (Perpendicular) to the longitudinal axis of the implant sample (n=4)

FIG. 4 shows that the anisotropic properties of a biocomposite plate are directly affected by fiber orientation, as demonstrated by the large difference in mechanical properties of samples with identical compositions, but with non-aligned layers (Amorphous) or with layers aligned at either 0° (Parallel) or 90° (Perpendicular) to the longitudinal axis of the implant sample (n=4). Table 2 summarizes the numerical results for mechanical properties;

TABLE 2

Mean values and standard deviations of statistically significant mechanical properties of the anisotropic implants. (n = 4).

|  | E [Mpa] | Flexural Strength [Mpa] | Max Load [N] | Density [gr/ml] | Volume [mm$^3$] |
|---|---|---|---|---|---|
| Amorphous | 3183.15 ± 396.7 | 56.56 ± 6.2 | 6.10 ± 0.73 | 1.46 ± 0.05 | 405.50 ± 49 |
| Parallel | 10572.5 ± 878.2 | 333.1 ± 32.8 | 41.74 ± 6.17 | 1.34 ± 0.066 | 447.67 ± 21 |
| Perpendicular | 483.47 ± 84.4 | 14.22 ± 0.76 | 2.13 ± 0.13 | 1.33 ± 0.021 | 487.26 ± 18.3 |
| Parallel to Amorphous Anisotropocity (%) | 332% | 589% | 684% | | |
| Parallel to Perpendicular Anisotropocity (%) | 2189% | 2342% | 1960% | | |
| Amorphous to Perpendicular Anisotropocity (%) | 659% | 398% | 286% | | |

TABLE 3

Mean values and standard deviations of tensile mechanical properties of the implants (n = 4).

| | E [MPa] | Tensile Strength [MPa] | Ultimate tensile strain [mm/mm] | Tensile Max Load [N] | Density [gr/ml] | Volume [mm3] |
|---|---|---|---|---|---|---|
| Tensile Plate (Parallel) | 7700.35 ± 594.7 | 89.65 ± 6.71 | 0.075 ± 0.01 | 752.5 ± 94.8 | 1.47 ± 0.03 | 428.66 ± 48.9 |
| Improvement in mechanical properties as tested in flexural axis as compared with mechanical properties as tested in tensile axis (% of flexural value divided by tensile value) | 137% | 372% | | | | |

Figure 5C:
FIGS. 5A-C show representative sample examples.
Figure 5B:
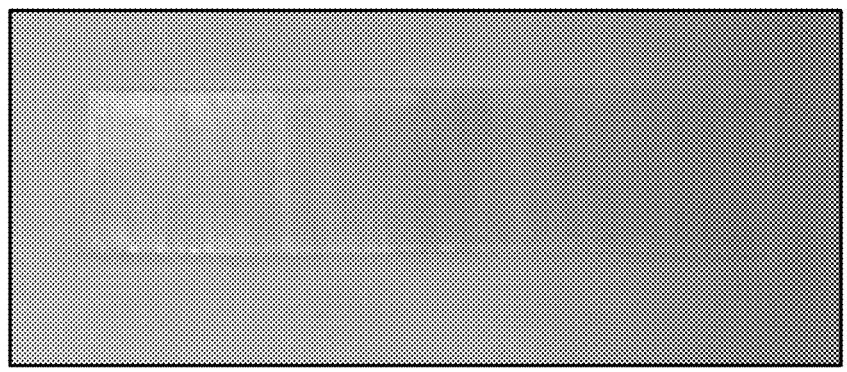
Figure 5A:
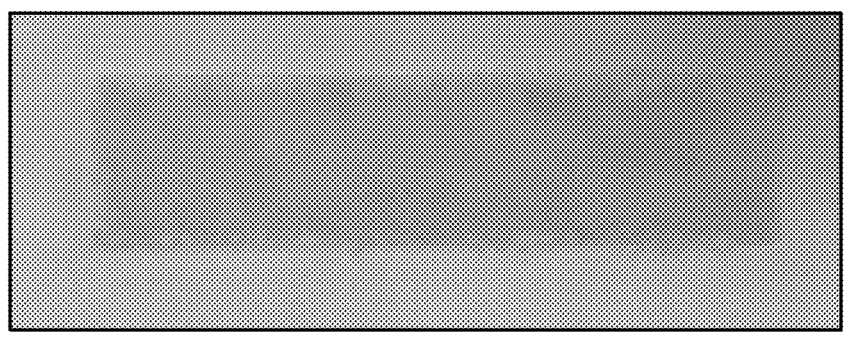

FIG. 5 shows representative sample examples. FIG. 5A shows an amorphous fiber orientation sample; FIG. 5B shows a sample with majority of layers with fiber orientation perpendicular to implant longitudinal axis. FIG. 5C shows a sample with majority of layers with fiber orientation parallel to implant longitudinal axis. Mechanical properties of sample C were superior to those of samples A and B; however sample A had properties that were superior to sample B, presumably due to the presence of at least some parallel fibers.

Example #3

Example 3 differs from Examples 1 and 2 in that identical material composites were used to produce rectangular plate implants but a different production method was used that resulted in a lower density. This examples shows that such samples with lower density have much inferior mechanical properties as compared with the otherwise similar higher density samples described in examples 1 and 2. Density changes are due to the production method. Without wishing to be limited by a single hypothesis, density depends on how much air or water is incorporated in the implant over the course of production.

Materials and Methods

Rectangular testing samples (dimensions 50.8 mm×12.7 mm×1.1 mm), simulating plates used for small bone fixation, were produced using reinforced composite material. Material composite was as described in Example 1.

Four testing samples were produced, manufactured by a two step process of 1) wrapping two complete layers of composite material around a 40 mm diameter tube using a hot air blower to adhere layers to each other and form a two layer biocomposite tube; 2) cutting biocomposite tube into two sheets and pressing sheets against each other using heated steel blocks. Each layer was 0.18 mm thick. The resulting samples were each comprised of the PLDLA polymer with embedded uni-directionally aligned continuous fibers where orientation of layers relative to longitudinal axis of implant were 8°, −8°, 8°, −8°. This specific alignment was designed to approximate 0° and would be expected to approximate the mechanical properties of the 0° (Parallel) samples described in example 2 if all other parameters were equal.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 0.942 mm/min (Dimensions, weight and density of samples were measured. Statistical comparison between two treatments was performed using a t-test. A confidence level of p=0.05 was used.

Results

Table 4 shows the significance of structural differences between reinforced composites. The alignment with 8 degree fiber offset described herein would be expected to be nearly identical to the parallel fiber alignment described in Example 1, and yet the strength and modulus are drastically lower. Without wishing to be limited by a single hypothesis, it is believed that the much lower density seen in this example (Example 3) was the cause or at least a significantly contributing factor.

TABLE 4

Mean values and standard deviations of the mechanical properties of the anisotropic implant. (n = 4).

| | E [MPa] | Flexural Strength [MPa] | Max Load [N] | Density [gr/ml] | Volume [mm³] |
|---|---|---|---|---|---|
| 4layers, 8deg | 2052.47 ± 96.55 | 49.24 ± 2 | 18.52 ± 0.43 | 0.935 ± 0.01 | 775.49 ± 17.11 |

Example #4

The below example describes how anisotropic biocomposite implants retain significant mechanical properties (modulus and strength) after exposure to rigorous accelerated degradation conditions.

Materials and Methods

Rectangular testing samples (dimensions 50.8 mm×12.7 mm×1.1 mm), simulating plates used for small bone fixation, were produced using reinforced composite material. Material composite was as described in Example 1.

Eight testing samples were produced, manufactured by compression molding of four or five layers of composite material. Each layer was 0.18 mm thick. In four samples, five layer samples were each comprised of the PLDLA polymer with embedded uni-directionally aligned continuous fibers where orientation of layers relative to longitudinal axis of implant were 0° (parallel to implant longitudinal axis), 45°, 0°, −45°, 0°. In four other samples, four layer samples were each comprised of the PLDLA polymer with embedded uni-directionally aligned continuous fibers where orientation of layers relative to longitudinal axis were 0° (parallel to implant longitudinal axis), 45°, −45°, 0°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.536 mm/min. Implants were tested either at time=0 or after incubation in simulated body fluid (SBF). SBF was comprised of: 142 Na+, 5 K+, 1.5 Mg 2+, 2.5 Ca2+, 147.8 Cl−, 4.2 HCO3−, 1 HPO43−, 0.5 SO4 2− mol/m3. Samples were incubated at either 60 or 50 degrees C. in a shaking incubator (Wis-30 shaking incubator, Witeg, Germany) at 30 rpm for 3-4 days.

Results

Figure 6:
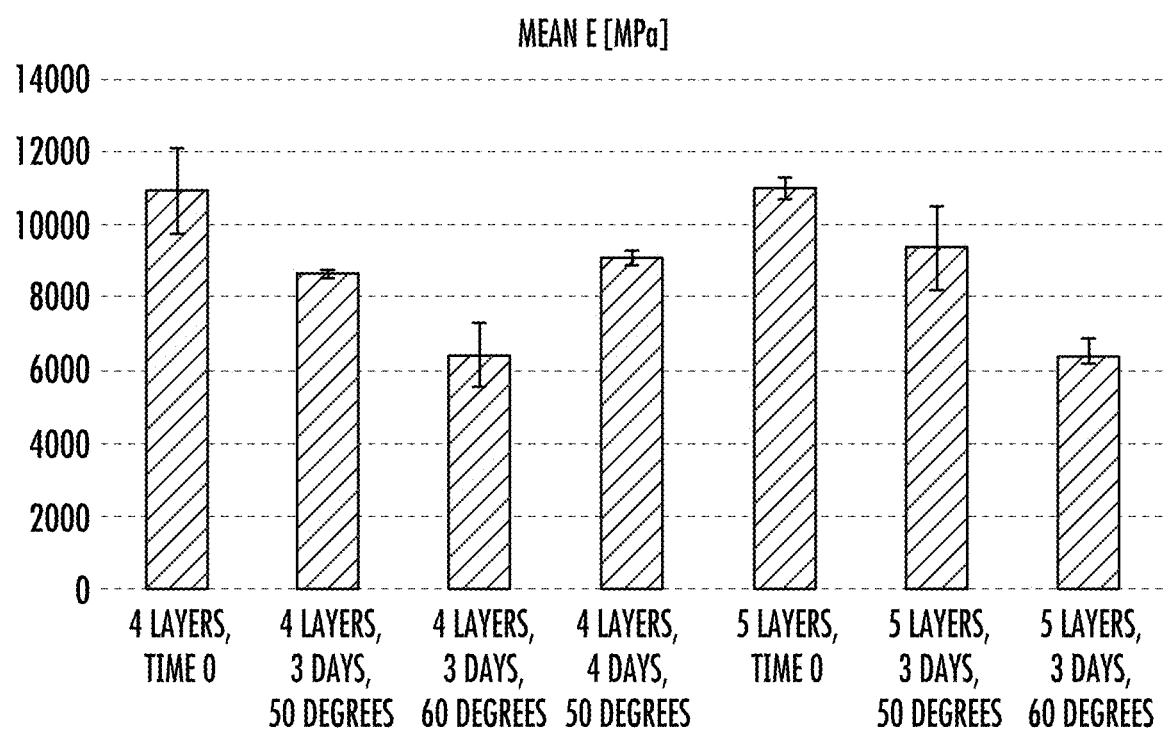
FIG. 6 shows elastic modulus after exposure of exemplary biocomposite samples to forced degradation.
Figure 7:
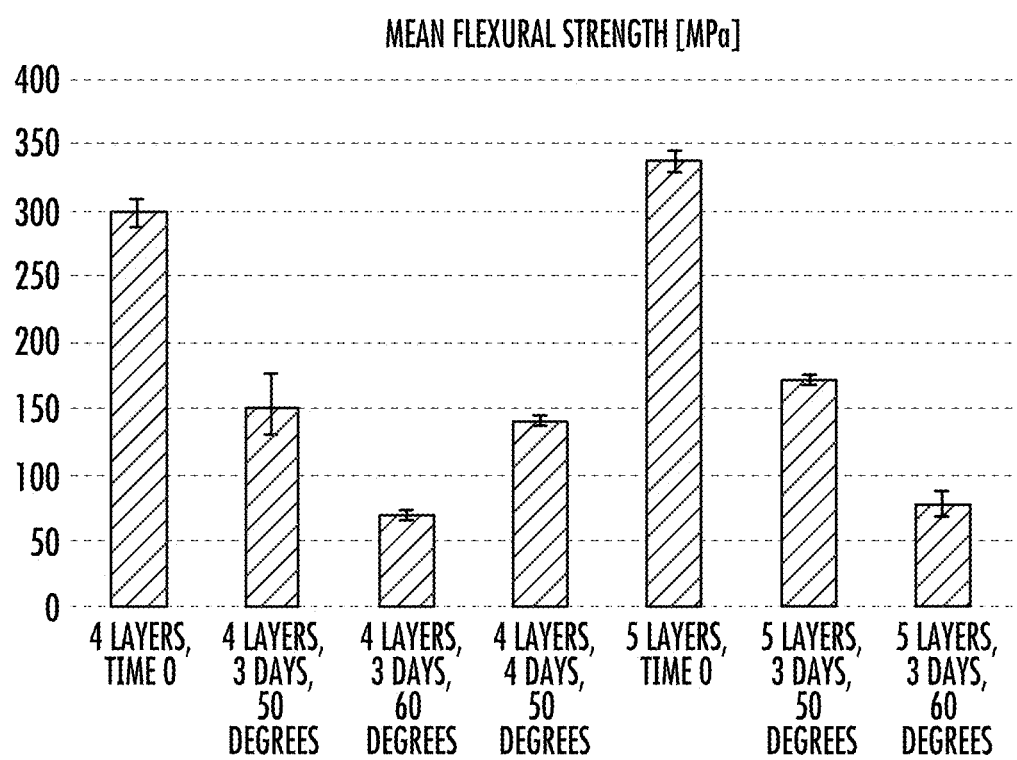
FIG. 7 shows flexural strength after exposure of exemplary biocomposite samples to forced degradation.

FIGS. 6 and 7: After exposure to accelerated degradation conditions of 50° C. for three days, both groups of samples retained >80% of their elastic modulus and >30% of their flexural strength. 50° C. is the highest indicative temperature for incubation conditions for accelerated degradation since the Tg of the biocomposite material is ~56 C.) FIG. 6 shows elastic modulus after exposure to forced degradation, while FIG. 7 shows flexural strength after exposure to forced degradation.

Example #5

Below example describes production of hollow pin implants with reinforced biocomposite materials. As with plates, hollow pins with alignment with anisotropic characteristics, result in higher mechanical properties in the desired bending force parameters.

Materials and Methods

Hollow pin implants of dimensions appropriate for small bone fixation (2 mm OD, 1 mm ID, 5 cm) were made of composite material of composition as described in Example 1. Pin implants were manufactured in two steps and two types of pin implants were produced: Parallel alignment and amorphous alignment.

For parallel alignment samples (n=7), plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. Two 5 cm length segments of plate were put into a tube mold such that parallel fiber orientation was also parallel to the longitudinal of the pin. The plate segments were thus molded into tube form to form tubes where orientation of layers relative to longitudinal axis of implant were 0° (parallel to implant longitudinal axis), 0°, 0°.

For amorphous alignment samples (n=3), plates of 0.5-0.6 mm were produced by compression molding three 0.18 mm thick layers of biocomposite material. Plates were each comprised of the PLDLA polymer with embedded continuous fibers that were not uni-directionally aligned but rather the layers were chopped into segments of approximately 3 mm and then molded together into the rectangular plates in bulk. Two 5 cm length segments of plate were put into a tube mold. The plate segments were thus molded into tube form to form tubes with amorphous alignment.

Implant pins samples were tested for Flexural strength, Elastic modulus and Maximum load according to modified ASTM D790-10 with a 500N load cell and a 3 point bending fixture (220Q1125-95, TestResources, MN, USA). Load span was 25.4 mm and cross head speed was set at 2 mm/min.

Flexural modulus was calculated according to:

$$\sigma_{max} = \frac{8 F_{max} L d_0}{\pi (d_0^4 - d_i^4)} \quad (1)$$

Where d0 is the outer diameter of the tube, di is the inner diameter of the tube and L is the support span.

Flexural Elastic modulus was calculated according to:

$$E = \frac{4 m L^3}{3\pi (d_0^4 - d_i^4)} \quad (2)$$

Results

Table 5 shows the numerical summary of the various mechanical parameters for the pins for material aligned in parallel, tested and then calculated as described above. Table 6 shows the corresponding results for amorphous (non-aligned) pins. With the exception of volume and density, pins made from the parallel aligned material had nearly four times as great mechanical properties as pins made from the amorphous material.

TABLE 5

Mean values and standard deviations of mechanical properties for parallel aligned pins as compared with amorphous (non-aligned) pins

| Sample | E [MPa] | Flexural Strength [MPa] | Density [gr/ml] | Max Load [N] | Volume [mm³] |
|---|---|---|---|---|---|
| Parallel Tubes (n = 7) | 8890.74 ± 1209.5 | 158.62 ± 19.3 | 1.47 ± 0.02 | 19.82 ± 3.2 | 121.88 ± 7.06 |
| Amorphous Tubes (n = 3) | 2907.13 ± 730.9 | 40.15 ± 7.8 | 1.35 ± 0.04 | 4.82 ± 0.68 | 138.52 ± 2.96 |
| Parallel to Amorphous Anisotropocity (%) | 306% | 395% | | | |

Figure 8A:
FIGS. 8A and 8B are photographs of a representative hollow pin implant, 5 cm length, 2 mm OD, 1 mm ID.
Figure 8B:

FIG. 8 is a photograph of a representative hollow pin implant, 5 cm length, 2 mm OD, 1 mm ID. FIG. 8A is a photo of the pin along its length; FIG. 8B is a photo of the cross-section of the pin.

Example #6

Below example describes production of reinforced biocomposite pin implants that are not hollow.

Materials and Methods

Pin implants of dimensions appropriate for small bone fixation (2 mm OD, 5 cm) were made of composite material of composition as described in Example 1. Pin implants were manufactured in two steps. Plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. Four 5 cm length segments of plate were put into a cylinder mold such that parallel fiber orientation was also parallel to the longitudinal of the pin. The plate segments were thus molded into cylinder form to form cylinders where orientation of layers relative to longitudinal axis of implant were 0° (parallel to implant longitudinal axis), 0°, 0°.

Implant pins were tested for Flexural strength, Elastic modulus and Maximum load according to modified ASTM D790-10 with a 500N load cell and a 3 point bending fixture (220Q1125-95, TestResources, MN, USA). Load span was 25.4 mm and cross head speed was set at 2 mm/min.

Flexural modulus was calculated according to:

$$\sigma_{max} = \frac{8F_{max}L}{\pi d_0^3} \quad (1)$$

Where $d_0$ is the outer diameter of the cylinder and L is the support span.

Flexural Elastic modulus was calculated according to:

$$E = \frac{4mL^3}{3\pi d_0^4} \quad (2)$$

Results

TABLE 7

Mean values and standard deviations of mechanical properties (n = 3).

| | E [MPa] | Flexural Strength [MPa] | Density [gr/ml] | Max Load [N] | Volume [mm³] |
|---|---|---|---|---|---|
| Full Cylinders | 9536.53 ± 1348.7 | 202.82 ± 90.7 | 1.403 ± 0.003 | 24.79 ± 10.12 | 169.58 ± 6.6 |

Figure 9A:
FIGS. 9A and 9B are photographs of a representative pin, 5 cm length, 2 mm OD.
Figure 9B:

FIG. 9 is a photograph of a representative pin, 5 cm length, 2 mm OD. FIG. 9A is a photo of the pin along its length; FIG. 9B is a photo of the cross-section of the pin.

Example #7

The below example describes how anisotropic biocomposite implants retain a high amount of mechanical properties (modulus and strength) after exposure to degradation conditions.

Materials and Methods

Rectangular testing samples (dimensions 50.8 mm×12.7 mm×0.75 mm), simulating plates used for small bone fixation, were produced using reinforced composite material. Material composite was as described in Example 1.

Samples were produced by compression molding of five layers of composite material. Each layer was 0.18 mm thick. Five layer samples were each comprised of the PLDLA polymer with embedded uni-directionally aligned continuous fibers where orientation of layers relative to longitudinal axis of implant were 0° (parallel to implant longitudinal axis), 45°, 0°, −45°, 0°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.536 mm/min. Implants were tested either at time=0 or after incubation in simulated body fluid (SBF). SBF was comprised of: 142 Na+, 5 K+, 1.5 Mg 2+, 2.5 Ca2+, 147.8 Cl−, 4.2 HCO3−, 1 HPO43−, 0.5 SO4 2− mol/m3. Samples were incubated in SBF at 37 degrees C. in a shaking incubator (Wis-30 shaking incubator, Witeg, Germany) at 30 rpm for five days.

Results

|  | E [MPa] | Flexural Strength [MPa] | Max Load [N] | Density [gr/ml] | Volume [mm³] |
|---|---|---|---|---|---|
| T₀ | 10859.44 ± 163.6 | 281.59 ± 2.97 | 43.37 ± 0.91 | 1.47 ± 0.002 | 479.33 ± 12.29 |
| 5 days, 37 C. | 9694.59 ± 1322.5 | 188.24 ± 39.85 | 37.84 ± 1.69 | 1.47 ± 0.03 | 550.05 ± 85.07 |

FIG. 10 shows the decrease in mechanical properties due to incubation under conditions that force degradation. These results show that after 5 days of simulated strength degradation, implants retained >60% of flexural strength, >85% of Modulus and Max load.

Additionally, implant swelling was measured following the incubation at 37 C for 5 days, with thickness of implants increasing by 1.9% and overall volume by 2.8%.

Example #8

The below example describes how anisotropic biocomposite implants retain a high amount of mechanical properties (modulus and strength) after exposure to degradation conditions.

Materials and Methods

Rectangular testing samples (dimensions 50.8 mm×12.7 mm×0.75 mm), simulating plates used for small bone fixation, were produced using reinforced composite material. Material composite was as described in Example 1.

Samples were produced by compression molding of five layers of composite material. Each layer was 0.18 mm thick. Five layer samples were each comprised of the PLDLA polymer with embedded uni-directionally aligned continuous fibers where orientation of layers relative to longitudinal axis of implant were 0° (parallel to implant longitudinal axis), 45°, 0°, −45°, 0°.

Implant samples were tested for Flexural strength, Elastic modulus and Maximum load according to ASTM D790-10 with a 500N load cell and a 3 point bending fixture (220Q1125-95, TestResources, MN, USA). Load span was 25.4 mm and cross head speed was set at 1.536 mm/min. Implants were tested either at time=0 or after incubation in simulated body fluid (SBF). SBF was comprised of: 142 Na+, 5 K+, 1.5 Mg 2+, 2.5 Ca2+, 147.8 Cl−, 4.2 HCO3−, 1 HPO43−, 0.5 SO4 2− mol/m3. Samples were incubated in SBF at 37 degrees C. in a shaking incubator (Wis-30 shaking incubator, Witeg, Germany) at 30 rpm for one day.

Results plates, hollow pins with alignment with anisotropic characteristics, result in higher mechanical properties in the desired bending force parameters.

Materials and Methods

Hollow pin implants of dimensions appropriate for small bone fixation (2 mm OD, 1 mm ID, 5 cm length) were made of composite material of composition as described in Example 1. Pin implants were manufactured in two steps and two types of pin implants were produced: hollow cylindrical pins and full cylindrical pins.

For hollow pins (n=3), plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. One 5 cm length segment of plate was put into each side of a tube mold (total of two segments) such that parallel fiber orientation was also parallel to the longitudinal of the pin. The plate segments were thus molded into tube form to form tubes where orientation of layers relative to longitudinal axis of implant were 0° (parallel to implant longitudinal axis), 0°, 0°.

For full cylindrical pins (n=3), plates of 0.5-0.6 mm were produced by compression molding three 0.18 mm thick layers of biocomposite material. Plates were each comprised of the PLDLA polymer with embedded uni-directionally aligned continuous fibers where orientation of layers relative to longitudinal axis of implant were 0° (parallel to implant longitudinal axis), 0°, 0°. Four 5 cm length segments of plate were put into a cylindrical mold such that parallel fiber orientation was also parallel to the longitudinal of the pin. The plate segments were thus molded into cylinder form to form cylinders where orientation of layers relative to longitudinal axis of implant were 0° (parallel to implant longitudinal axis), 0°, 0°.

Implant samples were tested for tensile strength, tensile modulus and maximum load according to modified ASTM D3039M with a 5 KN load cell and an appropriate fixture

|  | E [MPa] | Flexural Strength [MPa] | Max Load [N] | Density [gr/ml] | Volume [mm³] |
|---|---|---|---|---|---|
| T0 | 11416.92 ± 403.7 | 289.67 ± 20.9 | 88.45 ± 7.5 | 1.45 ± 0.05 | 668.49 ± 23.5 |
| 24 hrs, 37 C. | 11698.2 ± 502.5 | 260.05 ± 14.2 | 74.04 ± 5.25 | 1.50 ± 0.03 | 638.58 ± 55.2 |

After 24 hour incubation, there was no change in elastic modulus, >85% of flexural strength was retained, and >20% of max load.

Example #9

Below example describes production of hollow pin implants with reinforced biocomposite materials. As with (220Q1125-95, TestResources, MN, USA). Sample span was 30 mm at the beginning of the test and cross head speed was set at 2 mm/min. Dimensions, weight and density of samples were recorded.

Results

Perhaps unsurprisingly, measures of mechanical strength (including elastic module, tensile strength and max load) were all significantly higher for full (non-hollow) pins as compared to hollow pins, as shown in Tables 10 and 11.

TABLE 10

Mean values and standard deviations of mechanical properties of hollow pin implants (n = 3) and full pin implants (n = 3).

| | E [MPa] | Tensile strength [MPa] | Ultimate tensile strain [mm/mm] | Max Load [N] | Density [gr/ml] | Volume [mm3] |
|---|---|---|---|---|---|---|
| Hollow Pin Tensile | 8244.3 ± 1379.8 | 78.01 ± 32.6 | 0.026 ± 0.008 | 261.85 ± 113.3 | 1.41 ± 0.06 | 2.548 ± 0.17 |
| Full Pin Tensile | 10724.7 ± 969.7 | 132.9 ± 23.09 | 0.029 ± 0.002 | 431.77 ± 75.9 | 1.43 ± 0.03 | 3.25 ± 0.18 |

Notably, the ratio of modulus as tested in tensile testing between hollow pins and full pins was 0.77 and the ratio of tensile strength was 0.59. For similar pins, as described in examples 5 and 6, the ratio of modulus as tested in flexural testing between hollow pins and full pins was 0.93 and the ratio of flexural strength was 0.78. These results suggest that the same 25% loss in volume between a full and hollow cylindrical geometry results in a different effect on modulus and strength depending on the axis of mechanical testing (tensile or flexural). More strength and modulus are retained for bending resistance (flexural axis) than are retained for elongation resistance (tensile axis) in the hollow geometry.

Example #10

Composite material technology can result in performance unattainable by individual constituents, achieving diverse performance demands that could not be met by one material. A unique combination of strength, stiffness, density and degradation rate is achieved based on the structural composition and orientation of fibers inside the implants.

A mechanical simulations of fiber orientations and structural compositions using the above-described aligned reinforced biocomposite material was performed. The simulation suggested fiber orientations and structural compositions that best fit the bending force load conditions involved in many applications of orthopedic bone fixation. Biomechanical design of implant per clinical application allows for maximizing clinical benefit by reducing implant size and the amount of foreign material being implanted, achieving both required strengths and desired rate of implant absorption.

Figure 11B:
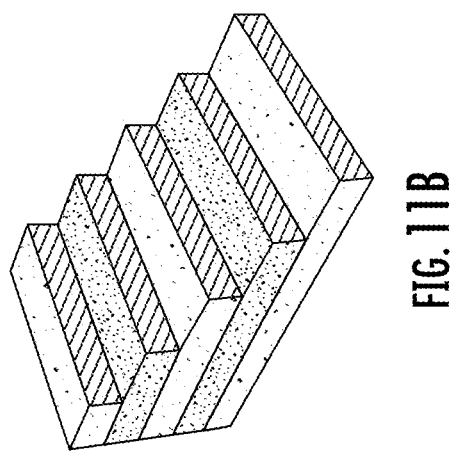
FIGS. 11A and 11B demonstrate a graphical finite elements simulation.
Figure 11A:
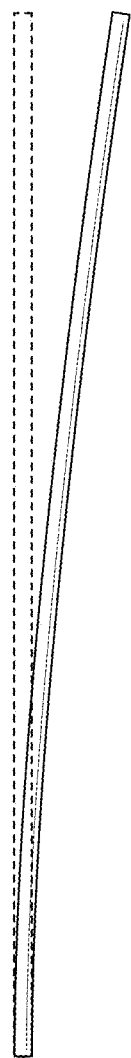

FIG. 11 shows a graphical finite elements simulation. FIG. 11A shows force distribution on a hollow cylinder pin implant with a wall thickness made of 5 layers as demonstrated in FIG. 11B.

Figure 1B:
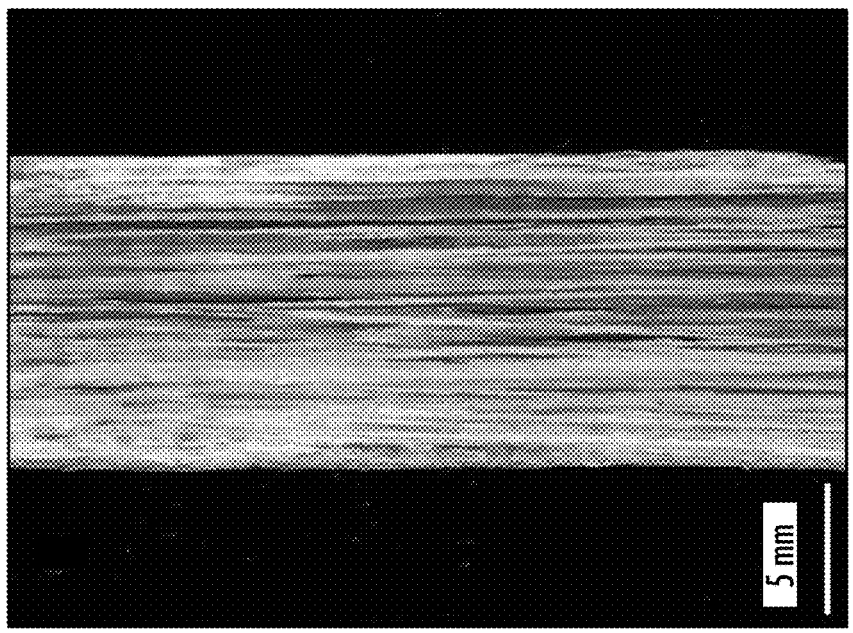
Figure 1A:
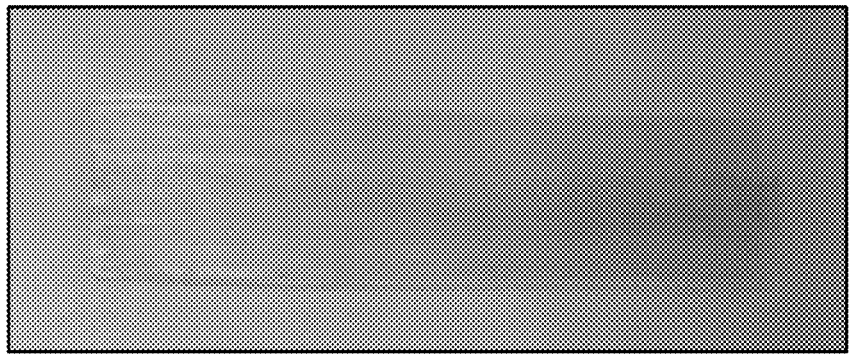

Finite element modeling on a hollow bone fixation pin was performed to evaluate possible layer set ups that can support the expected biomechanical load (FIG. 1). Exact fiber orientation per layer greatly affects the performance of an implant. Table 12 shows how an increase in 10 [N] for the buckling load of an implant in a single direction can be theoretically achieved using different layer structures.

TABLE 12

Finite element simulation results on a 2 mm pin implant for different layer configurations. Orientation presented as: inner (left) to outer (right). Simulation confirms that higher buckling loads can be reached when optimizing layer orientation. In this example optimizing can result in an increase in buckling load from 23 [N] to 32[N]

| Configuration | Bending stiffness [N/mm] | Buckling load [N] |
|---|---|---|
| 0/0/0/45/−45 | 0.554 | 22.7 |
| 45/0/0/0/−45 | 0.589 | 24.0 |
| 0/45/0/−45/0 | 0.591 | 24.2 |
| 45/−45/0/0/0 | 0.626 | 25.7 |
| 20/−20/20/−20/20 | 0.610 | 24.8 |
| 15/−15/15/−15/15 | 0.629 | 29.1 |
| 10/−10/10/−10/10 | 0.788 | 32.5 |

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. It will also be appreciated by persons skilled in the art that the present invention is not limited by what has been particularly shown and described hereinabove.

All references cited or described herein are hereby incorporated by reference as if set forth herein to the extent necessary to support the description of the present invention and/or of the appended claims.

Although the invention has been described in conjunction with specific embodiments thereof, it is evident that many alternatives, modifications and variations will be apparent to those skilled in the art. Accordingly, it is intended to additionally embrace all such alternatives, modifications and variations that fall within the spirit and broad scope of the appended claims.

What is claimed is:

1. An orthopedic implant comprising a biodegradable composite, the biodegradable composite comprising a reinforcement filler, wherein said reinforcement filler comprises a plurality of reinforcing fibers; wherein said biodegradable composite further comprises a biodegradable polymer; wherein an average density of the biodegradable composite is in a range of 1.3-3.0 g/cm$^3$; wherein an inherent viscosity (IV) of the biodegradable polymer alone is in the range of 1.0 to 3.0 dl/g; and wherein a percentage of reinforcing fibers is in the range of 40% to 50% weight per weight; wherein a plurality of said reinforcement fibers are arranged in parallel to a longitudinal axis of the implant.

2. The implant of claim 1, wherein the biodegradable composite has a maximum flexural modulus in the range of 6 GPa to 30 GPa and flexural strength in the range of 100 MPa to 1000 MPa.

3. The implant of claim 1, having improved mechanical properties in at least one mechanical axis or parameter as compared with at least one other mechanical axis or parameter within the same implant, such that the implant is anisotropic, wherein said mechanical parameter comprises one or more of bending strength and stiffness (resistance to bending force), tensile strength and stiffness (resistance to tensile force), compression strength and stiffness (resistance to compression force), shearing strength and stiffness (resistance to shearing force), or torsional strength and stiffness (resistance to torsional force) where in properties are anisotropic of at least 10%, 20%, 30%, 40%, 50%, 60%, 70%, 80%, 90% or 100%, or any number in between.

4. The implant of claim 1, wherein said biodegradable polymer comprises a homopolymer or a copolymer, wherein said copolymer comprises a random copolymer, block copolymer, or graft copolymer; and wherein said biodegradable polymer comprises a linear polymer, a branched polymer, or a dendrimer, of natural or synthetic origin; wherein said biodegradable polymer comprises lactide, glycolide, caprolactone, valerolactone, carbonates, dioxanones, δ-valerolactone, 1,dioxepanones, ethylene glycol, ethylene oxide, esteramides, y-hydroxyvalerate, β-hydroxypropionate, alpha-hydroxy acid, hydroxybutyrates, poly (ortho esters), hydroxy alkanoates, tyrosine carbonates, polyimide carbonates, polyimino carbonates, poly (bisphenol A-iminocarbonate) and poly (hydroquinone-iminocarbonate), polyurethanes, polyanhydrides, polymer drugs, sugars; starch, cellulose and cellulose derivatives, polysaccharides, collagen, chitosan, fibrin, hyaluronic acid, polypeptides, proteins, poly (amino acids), polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, lactide/glycolide/trimethylene carbonate terpolymers, lactide/glycolide/ε-caprolactone terpolymers, PLA/polyethylene oxide copolymers; polydepsipeptides; unsymmetrically-3,6-substituted poly-1,4-dioxane-2,5-diones; polyhydroxyalkanoates, polyhydroxybutyrates) PHB); PHB/b-hydroxyvalerate copolymers (PHB/PHV); poly-b-hydroxypropionate (PHPA); poly-p-dioxanone (PDS); poly-d-valerolactone-poly-ε-capralactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanoic acids; polycarbonates; polyorthoesters; polyphosphates; poly(ester anhydrides); and derivatives, copolymers and mixtures thereof.

5. The implant of claim 1, wherein the polymer is in a form of a polymer matrix, wherein said polymer matrix comprises a polymer selected from the group consisting of PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and a combination thereof.

6. The implant of claim 1, wherein if PLLA is used, the matrix comprises at least 30% 50%, or at least 70% PLLA, or wherein if PLDLA is used, the matrix comprises at least 5%, at least 10%, or at least 20% PLDLA.

7. The implant of claim 5, wherein an inherent viscosity (IV) of the polymer matrix alone is in the range of, 1.5 to 2.4 dl/g, or 1.6 to 2.0 dl/g.

8. The implant of claim 1, wherein an average fiber diameter is between 5 and 50 µm.

9. The implant of claim 8, wherein said fibers comprise one or more of a biodegradable glass or glass-like materials, a ceramic, a mineral composition (optionally including one or more of hydroxyapatite, tricalcium phosphate, calcium sulfate, calcium phosphate), a cellulosic material, a nanodiamond, or any other filler known in the art to increase the mechanical properties of a biodegradable polymer.

10. The implant of claim 9, wherein said biodegradable glass has oxide compositions in the following mol. % ranges (as a percent over the glass fiber composition):
$Na_2O$: 11.0-19.0 mol. %,
CaO: 9.0-14.0 mol. %,
MgO: 1.5-8.0 mol. %,
$B_2O_3$: 0.5-3.0 mol. %,
$Al_2O_3$: 0-0.8 mol. %,
$P_2O_5$: 0.1-0.8 mol. %,
$SiO_2$: 67-73 mol. %.

11. The implant of claim 10, wherein said ranges are the following mol. % ranges:
$Na_2O$: 12.0-13.0 mol. %,
CaO: 9.0-10.0 mol. %,
MgO: 7.0-8.0 mol. %,
$B_2O_3$: 1.4-2.0 mol. %,
$P_2O_5$: 0.5-0.8 mol. %,
$SiO_2$: 68-70 mol. %.

12. The implant of any of claim 8, wherein a tensile strength of the reinforcement fiber is in the range of 1200-2800 Mpa.

13. The implant of claim 1, wherein at least 50% of elastic modulus is retained following exposure to simulated body fluid (SBF) at 50° C. for 3 days, or at least 70% is retained, and even at least 80% is retained.

14. The implant of claim 1, wherein the implant is selected from the groups including bone fixation plates, intramedullary nails, joint (hip, knee, elbow) implants, spine implants, and other devices for such applications for fracture fixation, tendon reattachment, spinal fixation, and spinal cages.

15. The implant of claim 1, wherein a reinforcing fiber diameter is in a range of 2-40 um, 8-20 um, or 12-18 um (microns).

* * * * *